US008772478B2

(12) United States Patent
Clary et al.

(10) Patent No.: US 8,772,478 B2
(45) Date of Patent: Jul. 8, 2014

(54) BENZENESULFONAMIDE COMPOUNDS, METHOD FOR SYNTHESIZING SAME, AND USE THEREOF IN MEDICINE AS WELL AS IN COSMETICS

(75) Inventors: Laurence Clary, La Colle sur Loup (FR); Sandrine Chambon, Le Cannet (FR); Laurent Chantalat, Grasse (FR); Pascale Mauvais, Corniche des cougoulins (FR); Olivier Roye, Fayence (FR); Marlène Schuppli, Le Rouret (FR)

(73) Assignee: Galderma Research & Development, Biot (FR)

( * ) Notice: Subject to any disclaimer, the term of this patent is extended or adjusted under 35 U.S.C. 154(b) by 182 days.

(21) Appl. No.: 13/381,237

(22) PCT Filed: Jun. 28, 2010

(86) PCT No.: PCT/FR2010/051330
§ 371 (c)(1),
(2), (4) Date: Jan. 25, 2012

(87) PCT Pub. No.: WO2011/001088
PCT Pub. Date: Jan. 6, 2011

(65) Prior Publication Data
US 2012/0116072 A1  May 10, 2012

(30) Foreign Application Priority Data
Jun. 30, 2009  (FR) ...................... 09 54459

(51) Int. Cl.
C07D 401/02 (2006.01)
C07D 417/02 (2006.01)
C07D 207/46 (2006.01)
C07D 211/02 (2006.01)
C07D 223/12 (2006.01)
C07D 265/32 (2006.01)

(52) U.S. Cl.
USPC ............. 544/62; 544/105; 544/165; 540/481; 540/597; 540/606; 546/153; 546/193; 546/221; 548/550

(58) Field of Classification Search
USPC ........... 540/481, 597, 606; 544/62, 105, 165; 546/153, 193, 221; 548/550
See application file for complete search history.

(56) References Cited
U.S. PATENT DOCUMENTS
6,326,516 B1  12/2001  Levin et al.
2003/0130238 A1  7/2003  Sandanayaka et al.
2008/0085893 A1  4/2008  Yang et al.

FOREIGN PATENT DOCUMENTS

| WO | WO 96/00214 A1 | 1/1996 |
|---|---|---|
| WO | 97/18194 A1 | 5/1997 |
| WO | WO 97/22587 A1 | 6/1997 |
| WO | WO 98/16503 A2 | 4/1998 |
| WO | WO 98/16506 A1 | 4/1998 |
| WO | WO 98/16514 A1 | 4/1998 |
| WO | WO 98/16520 A1 | 4/1998 |
| WO | WO 00/44709 A2 | 8/2000 |
| WO | WO 2008/045671 A1 | 4/2008 |

OTHER PUBLICATIONS

Gueydan et al., "Avancees et perspectives de la recherche sur le facteur de necrose tumorale (TNF)", Med.Sci 1997, 13, 83-88.
Ortonne JP, "Prise en charge therapeutique du psoriasis en plaques: apport des anti-TNFα", Annales de dermatologie et de venereologie [Annals of dermatology and venereology], 2005, 132 (8-9 pt2), 4S6-9.
Aggarwal et al., "Tumor necrosis factors: Developments during the last decade", Eur. Cytokine Netw., 1996, 7: 93-124.
Mussi et al., "Serum TNF-alppha levels correlate with disease severity and are reduced by effective therapy in plaque-type psoriasis", J. Biol. Regul. Homeost Agents, 1997, 11, 115-118.
Thabet et al., "Drug evaluation: Apratastat, a novel TACE/MMP inhibitor for rheumatoid arthritis", Current Opinion in Investigational Drugs, Nov. 2006; 7(11), 1014-9.
International Search Report (PCT/ISA/210) issued on Oct. 26, 2010, by French Patent Office as the International Searching Authority for International Application No. PCT/FR2010/051330.
Written Opinion of the International Searching Authority (Form PCT/ISA/237) issued in PCT/FR2010/051330 on Jan. 4, 2012, and an English language translation of the Written Opinion.
Lohmander et al., "The Structure of Aggrecan Fragments in Human Synovial Fluid," Arthritis & Rheumatism, Sep. 1993, pp. 1214-1222, vol. 36, No. 9, American College of Rheumatology, US.
Schlöndorff et al., "Intracellular maturation and localization of the tumor necrosis factor α convertase (TACE)," Biochem. J., 2000, pp. 131-138, vol. 347, Biochemical Society, UK.
Black et al., "A metalloproteinase disintegrin that releases tumour-necrosis factor-α from cells," Nature, Feb. 20, 1997, pp. 729-733, vol. 385, Nature Publishing Group, UK.
Moss et al., "Cloning of a disintegrin metalloproteinase that processes precursor tumour-necrosis factor-α," Nature, Feb. 20, 1997, pp. 733-736, vol. 385, Nature Publishing Group, UK.
Tamura et al., "Highly Selective and Orally Active Inhibitors of Type IV Collagenase (MNP-9 and MMP-2): N-Sulfonylamino Acid Derivatives," J. Med. Chem., 1998, pp. 640-649, vol. 41, American Chemical Society, US.
MacPherson et al., "Discovery of CGS 27023A, a Non-Peptidic, Potent, and Orally Active Stromelysin Inhibitor That Blocks Cartilage Degradation in Rabbits," J. Med. Chem., 1997, pp. 2525-2532, vol. 40, American Chemical Society, US.

(Continued)

Primary Examiner — Kahsay Habte
(74) Attorney, Agent, or Firm — Dentons US LLP

(57) ABSTRACT

Benzenesulfonamide compounds having a structure of the following general formula (I) are described. Also described, are methods for synthesizing the compounds, and to the use thereof in pharmaceutical compositions for human or veterinary medicine and in cosmetic compositions.

20 Claims, No Drawings

(56) References Cited

OTHER PUBLICATIONS

Figure 1:
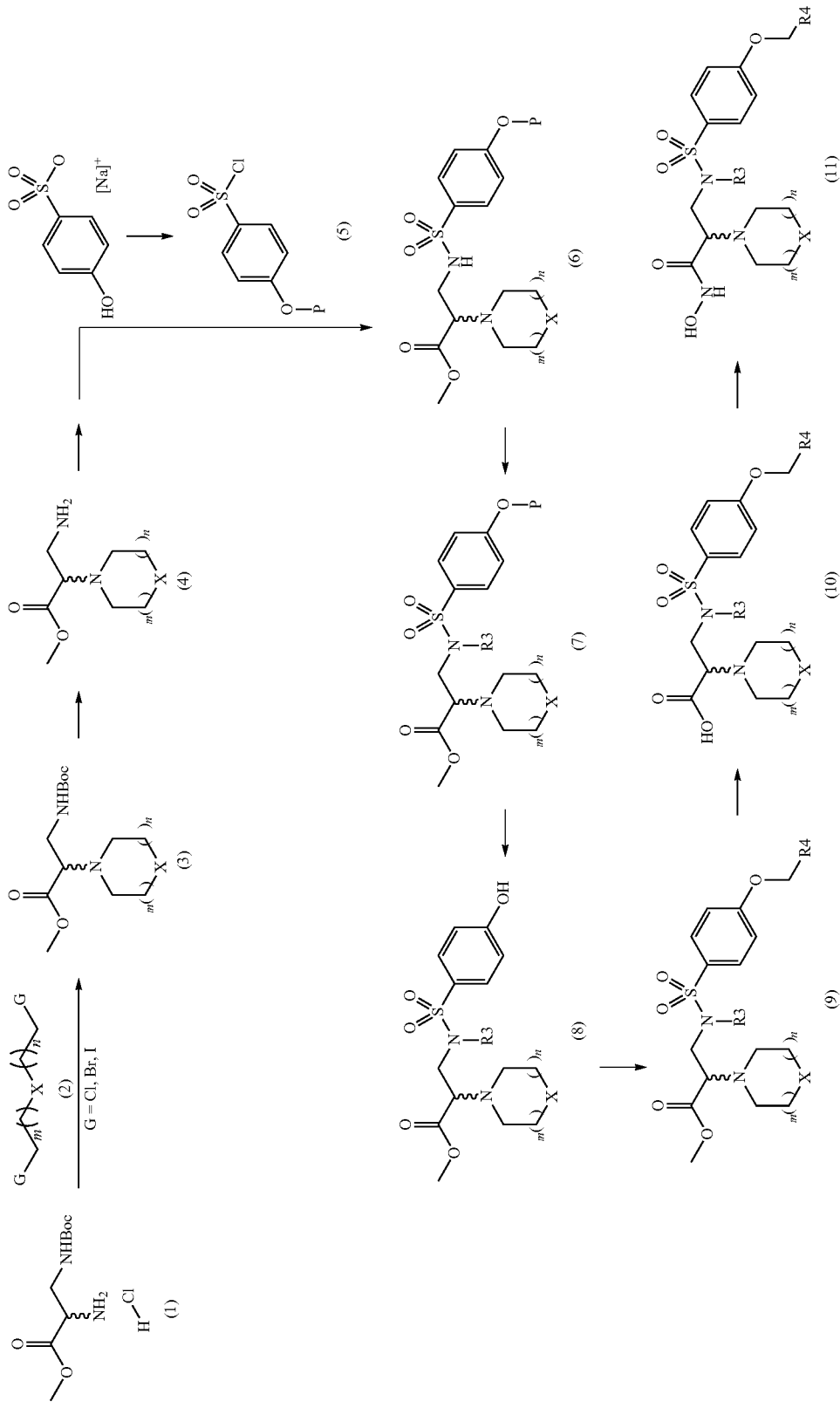

Kupper, "Immunologic Targets in Psoriasis," The New England Journal of Medicine, Nov. 20, 2003, pp. 1987-1990, vol. 349, Issue 21, Massachusetts Medical Society, US.

Bonifati et al., "Correlated increases of tumor necrosis factor-α, interleukin-6 and granulocyte monocyte-colony stimulating factor levels in suction blister fluids and sera of psoriatic patients-relationships with disease severity," Clinical and Experimental Dermatology, 1994, pp. 383-387, vol. 19, Wiley-Blackwell, UK.

MacDonald et al., "Tumour necrosis factor-alpha and interferon-gamma production measured at the single cell level in normal and inflamed human intestine," Clin. exp. Immunol., 1990, pp. 301-305, vol. 81, Blackwell Publishing, UK.

Elliot et al., "Randomised double-blind comparison of chimeric monoclonal antibody to tumour necrosis factor α (cA2) versus placebo in rheumatoid arthritis," The Lancet, Oct. 22, 1994, pp. 1105-1110, vol. 344, Elsevier, UK.

BENZENESULFONAMIDE COMPOUNDS, METHOD FOR SYNTHESIZING SAME, AND USE THEREOF IN MEDICINE AS WELL AS IN COSMETICS

This application claims priority under 35 U.S.C. §119 of FR 0954459, filed Jun. 30, 2009, and is the United States national phase of PCT/FR2010/051330, filed Jun. 28, 2010, and designating the United States (published in the French language on Jan. 6, 2011, as WO 2011/001088 A1; the title and abstract were also published in English), each hereby expressly incorporated by reference in its entirety and each assigned to the assignee hereof.

TECHNICAL FIELD

The present invention relates to novel benzenesulfonamide compounds corresponding to general formula (I) below:

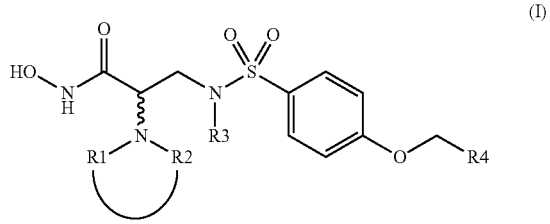

and also to the process for synthesizing same and to the use thereof in pharmaceutical compositions intended for use in human or veterinary medicine.

The compounds of the present invention act as inhibitors of TNFα-converting enzyme, also known as TACE. They are consequently of use in the treatment of diseases for which reducing TNFα production is of great interest.

The present invention also relates to the use of the compounds corresponding to general formula (I) in cosmetic compositions.

PRIOR ART

Adamalysins ("ADAM" or A Disintegrin and Metalloproteinase) are a subfamily of zinc metalloendopeptidase enzymes. Their ectodomain comprises a protease domain, the activation of which is zinc-dependent, a disintegrin domain and a cysteine-rich domain. To date, at least 30 different ADAMs have been identified, of which the first characterized was ADAM17, also known as TACE (TNFα-converting enzyme) [Gueydan C et al. Med. Sci 1997, 13, 83-88; Black R. A et al. Nature 1997, 385:729-733; Moss et al. Nature 1997, 385:733-736]. The TACE mRNA is present in many tissues and more particularly in monocytes, macrophages and T lymphocytes, but also in keratinocytes for example.

TACE is responsible for the cleavage of pro-TNFα, a 26 kDa membrane protein, so as to result in the release of biologically active soluble TNFα, a 17 kDa protein [Schlondorff et al. Biochem. J. 2000, 347, 131-138]. The soluble TNFα released by the cell is capable of acting on sites very remote from the site of synthesis.

TNFα is involved in a large number of pro-inflammatory biological processes [Aggarwal et al, Eur. Cytokine Netw., 1996, 7: 93-124]. Several pharmacological and clinical studies have shown in an obvious manner that blocking the effects of TNFα with specific anti-TNFα antibodies or anti-TNFα biologicals (Etanercept, Adalimumab, Infliximab) is beneficial in the treatment of autoimmune diseases such as rheumatoid arthritis [Feldman et al. Lancet, 1994, 344, 1105], non-insulin-dependent diabetes mellitus [Lohmander L. S et al. Arthritis Rheum, 1993, 36, 1214-1222], or Crohn's disease [MacDonald et al. Clin. Exp. Immunol. 1990, 81, 301].

TNFα also plays a fundamental role during the inflammatory phenomenon triggered in psoriasis lesions. Serum TNFα levels are elevated in psoriatic patients [Mussi A et al. J. Biol. Regul. Homeost Agents, 1997, 11, 115-118]; TNFα levels are also elevated in the actual psoriasis plaques [Bonifati C. et al. Clin. Exp. Dermatol., 1994, 19, 383-387]. The key cells in the physiopathology of psoriasis are keratinocytes, dendritic cells and certain T lymphocytes. The interaction between these families of cells results in an inflammatory cascade that leads to the characteristic psoriasis lesions with release of TNFα [Kupper T S, N. Engl. J. Med, 2003, 349, 1987-1990]. Clinical studies for the treatment of moderate to severe plaque psoriasis with anti-TNFα biologicals (Etanercept, Adalimumab, Infliximab) have demonstrated their efficacy both on psoriatic lesions and on the quality of life of the patients [Ortonne J P, Annales de dermatologie et de vénéreologie [Annals of dermatology and venereology], 2005, 132 (8-9 pt2), 4S6-9 and 2005, 132, 9S01-9S70]

Thus, compounds which inhibit TNFα production are of great interest for the treatment of inflammatory diseases and diseases involving TNFα release.

SUMMARY OF THE INVENTION

Our invention therefore describes novel molecules which inhibit the TACE enzyme (TNFα-converting enzyme) and, as a result, inhibit the secretion of soluble TNFα (active form of TNFα) by cells. These novel molecules are therefore potential active ingredients for the treatment of pathological conditions involving a decrease or an inhibition of TNFα production.

By way of illustration, and in a nonlimiting manner, these pathological conditions are, for example, septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, ischemic attack, transplant rejection, cancer, atherosclerosis, obesity, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), occular inflammation, inflammatory skin diseases, psoriasis, atopic dermatitis and psoriatic arthritis.

These molecules are also potential active ingredients for the treatment of neurological pathological conditions with an inflammatory nature, for which reducing TNFα production would be of great interest. These pathological conditions listed hereinafter in a nonlimiting manner are, for example, Alzheimer's disease, Parkinson's disease, parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barre syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke.

A large variety of TACE inhibitors is already known (see below). However, a large number of these inhibitors do not act selectively on the TACE enzyme compared with other enzymes of the family of ADAMs and/or of matrix metalloproteinases (MMPs).

As it happens, the nonselective inhibition of these enzyme families induces adverse side effects observed in viva For example, the inhibition of MMP-1 (collagenase-1) has been associated with musculoskeletal toxicity problems. As a nonselective inhibitor, mention may also be made of Apratastat, a known inhibitor tested clinically in phase 2 for the treatment of rheumatoid arthritis (Curr Opin Investig Drugs. 2006 November; 7(11),1014-9). This inhibitor is not selective for the TACE enzyme compared with certain MMPs (WO 00/44709; page 251, table 10, example 61).

Other TACE inhibitors which are also known and are part of the same family as Apratastat, namely the family of cyclic benzenesulfonamide derivatives, have been described in WO 00/44709 and WO 97/18194. Other patents (WO 96/00214, WO 97/22587) claim MMP and/or TACE inhibitors for which the benzenesulfonamide component is separated from the hydroxamic acid function by a single carbon atom. Publications describing MMP inhibitors of this type more broadly are also the publication by MacPherson et al., J. Med. Chem. 1997, 40, 2525 and the publication by Tamura et al., J. Med. Chem. 1998, 41, 640. Other examples of MMP/TACE inhibitors for which the sulfonamide function is separated from the hydroxamic acid by a series of two carbon atoms forming a ring are described in patents WO 98/16503, WO 98/16506, WO 98/16514 and WO 98/16520. Other examples of MMP inhibitors for which the sulfonamide function is separated from the hydroxamic acid by a series of two carbon atoms are also described in WO 2008/045671.

As it happens, the applicant has now discovered, unexpectedly and surprisingly, that novel compounds of general formula (I) exhibit a very good TACE-inhibiting activity, and in particular inhibit the TACE enzyme selectively compared with other ADAMs and MMPs.

Thus, the present invention relates to compounds of general formula (I) below:

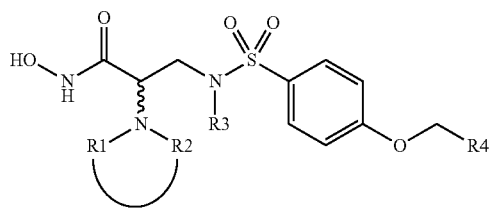

(I)

in which:

$R_1$ and $R_2$ are identical or different and represent alkyl radicals or else they form a ring with the nitrogen atom to which they are attached, said ring being represented by the formula below:

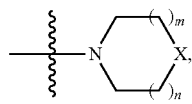

X, m and n having the meanings given hereinafter, $R_3$ is a hydrogen atom or a lower alkyl radical;

$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical or a substituted heteroaralkyl radical;

X represents an oxygen atom, a —$CH_2$— radical, a —CH—($CH_2$)p-$NR_5R_6$ radical, a sulfur atom, an SO radical or an $SO_2$ radical, $R_5$, $R_6$ and p having the meanings given hereinafter;

$R_5$ and $R_6$, which may be identical or different, represent a hydrogen atom, an alkyl radical, a substituted alkyl radical, an aryl radical or a substituted aryl radical;

m can take the values of 0 or 1;

n can take the values of 0, 1, 2 or 3;

p can take the values of 0, 1 or 2;

and also the addition salts of the compounds of general formula (I) with a pharmaceutically acceptable acid, the addition salts of the compounds of general formula (I) with a pharmaceutically acceptable base, and the enantiomers of the compounds of general formula (I).

Among the addition salts of the compounds of general formula (I) with a pharmaceutically acceptable acid, mention may preferably be made of the salts with an organic acid or with an inorganic acid.

The suitable inorganic acids are, for example, hydrohalic acids such as hydrochloric acid or hydrobromic acid, sulfuric acid, nitric acid and phosphoric acid.

The suitable organic acids are, for example, acetic acid, trifluoroacetic acid, trichloroacetic acid, propionic acid, glycolic acid, pyruvic acid, succinic acid, benzoic acid, cinnamic acid, mandelic acid, methanesulfonic acid, para-toluenesulfonic acid, salicylic acid, picric acid, citric acid, oxalic acid, tartaric acid, malonic acid, maleic acid, camphorsulfonic acid and fumaric acid.

Among the addition salts of the compounds of general formula (I) with a pharmaceutically acceptable base, mention may preferably be made of the salts with an organic base or with an inorganic base.

The suitable inorganic bases are alkali metal hydroxides or alkaline-earth metal hydroxides. Among these bases, mention may, for example, be made of potassium hydroxide, sodium hydroxide, lithium hydroxide or else calcium hydroxide.

The suitable organic bases comprise amines and amino acids. Among the amines, mention may, for example, be made of aliphatic or aromatic, primary, secondary or tertiary amines, such as methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline or isoquinoline.

Among the amino acids, mention may, for example, be made of lysine, arginine and ornithine.

According to the present invention, the term "lower alkyl radical" denotes a linear or branched, saturated hydrocarbon-based chain containing from 1 to 4 carbon atoms.

According to the present invention, the term "alkyl radical" denotes a linear or branched, saturated hydrocarbon-based chain containing from 1 to 10 carbon atoms.

According to the present invention, the term "alkenyl radical" denotes a linear or branched, unsaturated hydrocarbon-based chain containing from 2 to 10 carbon atoms and comprising one or more double bonds.

According to the present invention, the term "alkynyl radical" denotes a linear or branched, unsaturated hydrocarbon-based chain containing from 2 to 10 carbon atoms and comprising one or more triple bonds.

According to the present invention, the term "substituted alkyl radical" denotes a linear or branched, saturated hydrocarbon-based chain containing from 1 to 10 carbon atoms and substituted with one or more radicals chosen from a halogen atom, an alkoxy radical and a hydroxyl radical.

According to the present invention, the term "substituted alkenyl radical" denotes a linear or branched, unsaturated hydrocarbon-based chain containing from 2 to 10 carbon atoms, comprising one or more double bonds and substituted with one or more radicals chosen from a halogen atom, an alkoxy radical and a hydroxyl radical.

According to the present invention, the term "substituted alkynyl radical" denotes a linear or branched, unsaturated hydrocarbon-based chain containing from 2 to 10 carbon atoms, comprising one or more triple bonds and substituted with one or more radicals chosen from a halogen atom, an alkoxy radical and a hydroxyl radical.

According to the present invention, the term "cycloalkyl" denotes a cyclic saturated hydrocarbon-based chain containing from 3 to 7 carbon atoms.

According to the present invention, the term "substituted cycloalkyl" denotes a cyclic saturated hydrocarbon-based chain containing from 3 to 7 carbon atoms and substituted with one or more radicals chosen from a halogen atom, an alkoxy radical and a hydroxyl radical.

According to the present invention, the term "aryl radical" denotes an aromatic hydrocarbon-based ring or two fused aromatic hydrocarbon-based rings.

The preferred aryl radicals are chosen from phenyl and naphthyl radicals.

According to the present invention, the term "substituted aryl radical" denotes an aromatic hydrocarbon-based ring or two fused aromatic hydrocarbon-based rings which is (are) substituted with one or more groups of atoms chosen from an alkyl, an alkoxy, an aryl, a halogen, a hydroxyl, a cyano, a trifluoromethyl and a nitro.

According to the present invention, the term "aralkyl radical" denotes an alkyl substituted with an aryl.

According to the present invention, the term "substituted aralkyl radical" denotes an alkyl substituted with a substituted aryl.

According to the present invention, the term "heterocyclic radical" denotes a saturated or unsaturated, cyclic or polycyclic hydrocarbon-based chain comprising one or more heteroatoms chosen from O, S and N.

According to the present invention, the term "substituted heterocyclic radical" denotes a heterocyclic radical substituted with one or more groups of atoms chosen from an alkyl, an alkoxy, a halogen, a hydroxyl, a cyano, a trifluoromethyl and a nitro.

According to the present invention, the term "heteroaryl radical" denotes an aromatic heterocyclic radical, i.e. a cyclic or polycyclic aromatic hydrocarbon-based chain, comprising one or more heteroatoms chosen from O, S and N.

According to the present invention, the term "substituted heteroaryl radical" denotes a heteroaryl radical substituted with one or more groups of atoms chosen, for example, from an alkyl, an alkoxy, an aryl, a substituted aryl, a halogen, a hydroxyl, a cyano, a trifluoromethyl and a nitro.

According to the present invention, the term "heteroaralkyl radical" denotes an alkyl radical substituted with a heteroaryl radical.

According to the present invention, the term "substituted heteroaralkyl radical" denotes a heteroaralkyl radical substituted with one or more groups of atoms chosen from an alkyl, an alkoxy, a halogen, a hydroxyl, a cyano, a trifluoromethyl and a nitro.

According to the present invention, the term "alkoxy radical" denotes an oxygen atom substituted with an alkyl radical.

According to the present invention, the term "halogen atom" denotes a fluorine, chlorine, bromine or iodine atom.

Among the compounds of general formula (I) which fall within the context of the present invention, mention may in particular be made of the following compounds:

1) (S)-3-(4-benzyloxybenzenesulfonylamino)-N-hydroxy-2-piperidin-1-ylpropionamide
2) (S)-3-(4-benzyloxybenzenesulfonylamino)-N-hydroxy-2-pyrrolidin-1-ylpropionamide
3) (S)-3-[4-(4-fluorobenzyloxy)benzenesulfonylamino]-N-hydroxy-2-piperidin-1-ylpropionamide
4) (S)-3-[(4-benzyloxybenzenesulfonyl)methylamino]-N-hydroxy-2-piperidin-1-ylpropionamide
5) (S)—N-hydroxy-3-[4-(naphthalen-2-ylmethoxy)benzenesulfonylamino]-2-piperidin-1-ylpropionamide
6) (S)-3-[4-(3,4-dichlorobenzyloxy)benzenesulfonylamino]-N-hydroxy-2-piperidin-1-ylpropionamide
7) (S)-3-(4-benzyloxybenzenesulfonylamino)-N-hydroxy-2-morpholin-4-ylpropionamide
8) (S)—N-hydroxy-3-[4-(2-methylquinolin-4-ylmethoxy)benzenesulfonylamino]-2-piperidin-1-yl-propionamide
9) (S)-3-[4-(3,5-dichlorobenzyloxy)benzenesulfonylamino]-N-hydroxy-2-piperidin-1-ylpropionamide
10) (S)—N-hydroxy-2-piperidin-1-yl-3-(4-propoxybenzenesulfonylamino)propionamide
11) (S)-3-(4-cyclopropylmethoxybenzenesulfonylamino)-N-hydroxy-2-morpholin-4-ylpropionamide
12) (S)-3-[4-(4-tert-butylbenzyloxy)benzenesulfonylamino]-N-hydroxy-2-morpholin-4-ylpropionamide
13) (S)—N-hydroxy-2-morpholin-4-yl-3-(4-phenethyloxybenzenesulfonylamino)propionamide
14) (S)—N-hydroxy-3-[4-(2-methylquinolin-4-ylmethoxy)benzenesulfonylamino]-2-morpholin-4-yl-propionamide
15) (S)—N-hydroxy-3-[4-(2-methylquinolin-4-ylmethoxy)benzenesulfonylamino]-2-piperidin-1-yl-propionamide dihydrochloride
16) (R)—N-hydroxy-3-[4-(2-methylquinolin-4-ylmethoxy)benzenesulfonylamino]-2-pyrrolidin-1-yl-propionamide
17) (R)—N-hydroxy-3-[4-(2-methylquinolin-4-ylmethoxy)benzenesulfonylamino]-2-piperidin-1-yl-propionamide
18) (S)—N-hydroxy-3-[4-(2-methylquinolin-4-ylmethoxy)benzenesulfonylamino]-2-thiomorpholin-4-yl-propionamide
19) (S)-2-(1,1-dioxothiomorpholin-4-yl)-N-hydroxy-3-[4-(2-methylquinolin-4-ylmethoxy)benzene-sulfonylamino]propionamide
20) (S)-2-diethylamino-N-hydroxy-3-[4-(2-methylpyridin-4-ylmethoxy)benzenesulfonylamino]-propionamide 21) (S)-3-[4-(2,6-dimethylpyridin-4-ylmethoxy)benzenesulfonylamino]-2-(ethylpropylamino)-N-hydroxy-propionamide
22) (S)-2-azepan-1-yl-N-hydroxy-3-[4-(3-methylbenzyloxy)benzenesulfonylamino]propionamide
23) (S)-2-azepan-1-yl-N-hydroxy-3-[4-(2-methylquinolin-4-ylmethoxy)benzenesulfonylamino]-propionamide
24) (S)—N-hydroxy-2-piperidin-1-yl-3-[4-(pyrazolo[1,5-a]pyridin-3-ylmethoxy)benzenesulfonylamino]-propionamide
25) (S)—N-hydroxy-3-[4-(2-methylpyrazolo[1,5-a]pyridin-3-ylmethoxy)benzenesulfonylamino]-2-piperidin-1-yl-propionamide
26) (S)—N-hydroxy-2-piperidin-1-yl-3-[4-(quinolin-4-ylmethoxy)benzenesulfonylamino]propionamide
27) (S)—N-hydroxy-2-morpholin-4-yl-3-[4-(quinolin-4-ylmethoxy)benzenesulfonylamino]propionamide
28) (S)—N-hydroxy-3-{propyl[4-(quinolin-4-ylmethoxy)benzenesulfonyl]amino}-2-pyrrolidin-1-yl-propionamide
29) (S)-2-diethylamino-N-hydroxy-3-[4-(quinolin-4-ylmethoxy)benzenesulfonylamino]propionamide
30) (S)—N-hydroxy-3-[4-(3-methylbenzyloxy)benzenesulfonylamino]-2-[1,4]-oxazocan-4-yl-propionamide
31) (S)-2-azocan-1-yl-N-hydroxy-3-[4-(pyrimidin-4-ylmethoxy)benzenesulfonylamino]propionamide
32) (S)—N-hydroxy-2-morpholin-4-yl-3-[4-(pyrazolo[1,5-a]pyridin-3-ylmethoxy)benzenesulfonylamino]-propionamide
33) (S)—N-hydroxy-3-[4-(pyrazolo[1,5-a]pyridin-3-ylmethoxy)benzenesulfonylamino]-2-thiomorpholin-4-yl-propionamide
34) (S)—N-hydroxy-2-piperidin-1-yl-3-[4-(4-propoxybenzyloxy)benzenesulfonylamino]propionamide
35) (R)—N-hydroxy-3-[4-(2-methylquinolin-4-ylmethoxy)benzenesulfonylamino]-2-morpholin-4-yl-propionamide.
36) (S)-2-(4-ethylaminopiperidin-1-yl)-N-hydroxy-3-[4-(2-methylquinolin-4-ylmethoxy)benzene-sulfonylamino]propionamide
37) (S)-2-(3-aminopyrrolidin-1-yl)-N-hydroxy-3-[4-(2-methylquinolin-4-ylmethoxy)benzene-sulfonylamino]propionamide
38) (S)-2-(3-dimethylaminomethylpyrrolidin-1-yl)-N-hydroxy-3-[4-(2-methylquinolin-4-ylmethoxy)-benzene-sulfonylamino]propionamide
39) (S)-2-(4-benzylaminopiperidin-1-yl)-N-hydroxy-3-[4-(2-methylpyridin-4-ylmethoxy)benzene-sulfonylamino]propionamide
40) (S)—N-hydroxy-3-[4-(2-methyl-1H-indol-3-ylmethoxy)benzenesulfonylamino]-2-piperidin-1-yl-propionamide
41) (S)—N-hydroxy-3-[4-(2-isopropylbenzofuran-3-ylmethoxy)benzenesulfonylamino]-2-morpholin-4-yl-propionamide
42) (S)-2-azetidin-1-yl-N-hydroxy-3-[4-(2-methylquinolin-4-ylmethoxy)benzenesulfonylamino]-propionamide.

The compounds of general formula (I) in which R1 and R2 form a ring with the nitrogen atom to which they are attached are prepared according to the reaction scheme of figure 1 presented below.

According to figure 1, the compounds (3) are obtained by reaction between the amino acid (1) H-DAP(Boc)-OMe.HCl or H-(D)-DAP(Boc)-OMe.HCl and the compound (2) (commercial or prepared beforehand) in the presence of an organic tertiary base such as diisopropylethylamine or triethylamine at a temperature of between 60° C. and 120° C. The compounds (4) are obtained by deprotection of the amine function of the compounds (3) according to conventional methods such as, for example, the use of a solution of hydrochloric acid in isopropanol.

A reaction between the compound (4) and 4-hydroxybenzenesulfonyl chloride O-protected with a benzyl group (5) in the presence of a tertiary base such as, for example, triethylamine in dichloromethane, produces the compound (6). An N-alkylation of the sulfonamide function can then be carried out by reaction with an alkyl halide in the presence of a base such as, for example, potassium carbonate in a solvent such as DMF, so as to give the derivative (7). The compound (8) is obtained by deprotection according to methods known by those skilled in the art for deprotecting a phenol function. The compound (9) is obtained by alkylation of the phenol function of the compound (8) by reaction with an alkyl halide in the presence of a base such as, for example, cesium carbonate in acetone, or via a Mitsunobu reaction with a primary alcohol derivative in the presence of triphenylphosphine and of diisopropyl azodicarboxylate for example. The compound (10) is obtained via a saponification reaction in the presence of a base such as lithium hydroxide in the presence of water and of tetrahydrofuran for example. In a final step, the compound (11) is obtained by coupling between O-(tert-butyldimethylsilyl)hydroxylamine for example and the derivative (10) under conventional peptide coupling conditions, using, for example, 1-(3-dimethylaminopropyl)-3-ethylcarbodiimide hydrochloride, hydroxybenzotriazole or TBTU as coupling agents, and triethylamine or diisopropylethylamine as base, in a solvent such as dichloromethane or dimethylformamide. The deprotection of the silylated hydroxamic acid intermediately formed is carried out in situ or by washing with an acidic aqueous solution, so as to give the compound (11).

Another alternative for obtaining the compound (11) is presented in figure 2 below.

Figure 2:
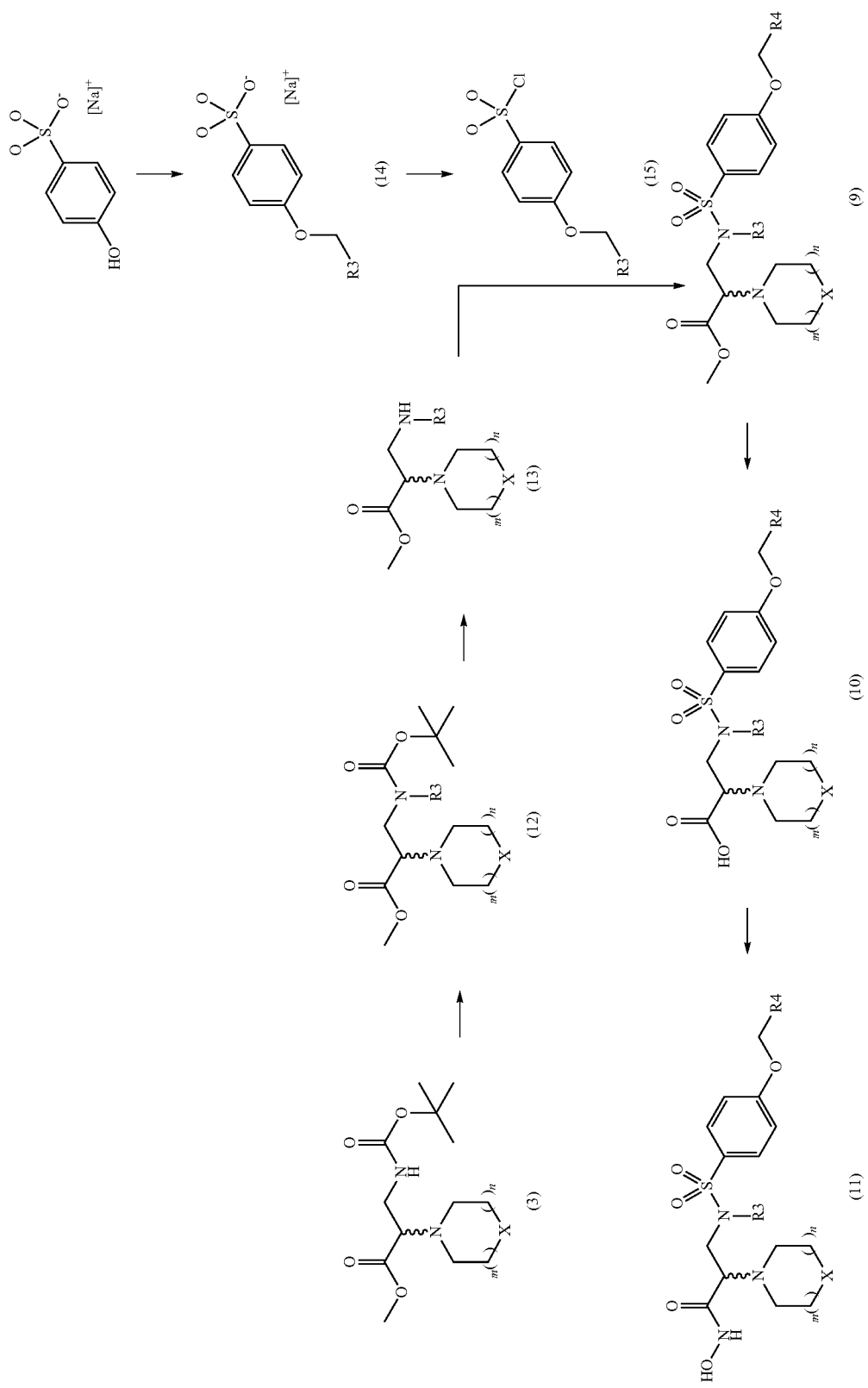

According to the synthesis scheme of figure 2, the derivative (3) can optionally be alkylated in the presence of a base such as sodium hydride and of an alkyl halide in dimethylformamide, for example, so as to give the compound (12), from which the compound (13) is obtained according to conventional methods for deprotecting amines, for instance the use of a solution of hydrochloric acid in isopropanol. The compound (14) is prepared beforehand from the commercially available 4-hydroxybenzenesulfonic acid sodium salt by alkylation with an alkyl halide in the presence of a base such as sodium hydroxide, for example, in a mixture of solvents such as isopropanol and water, for example. The compound (15) is then obtained by reacting the derivative (14) with oxalyl chloride in the presence of dimethylformamide in dichloromethane, for example.

The derivative (9) is obtained by reaction between the compounds (13) and (15) in the presence of a base such as triethylamine in dichloromethane, for example.

Figure 3:
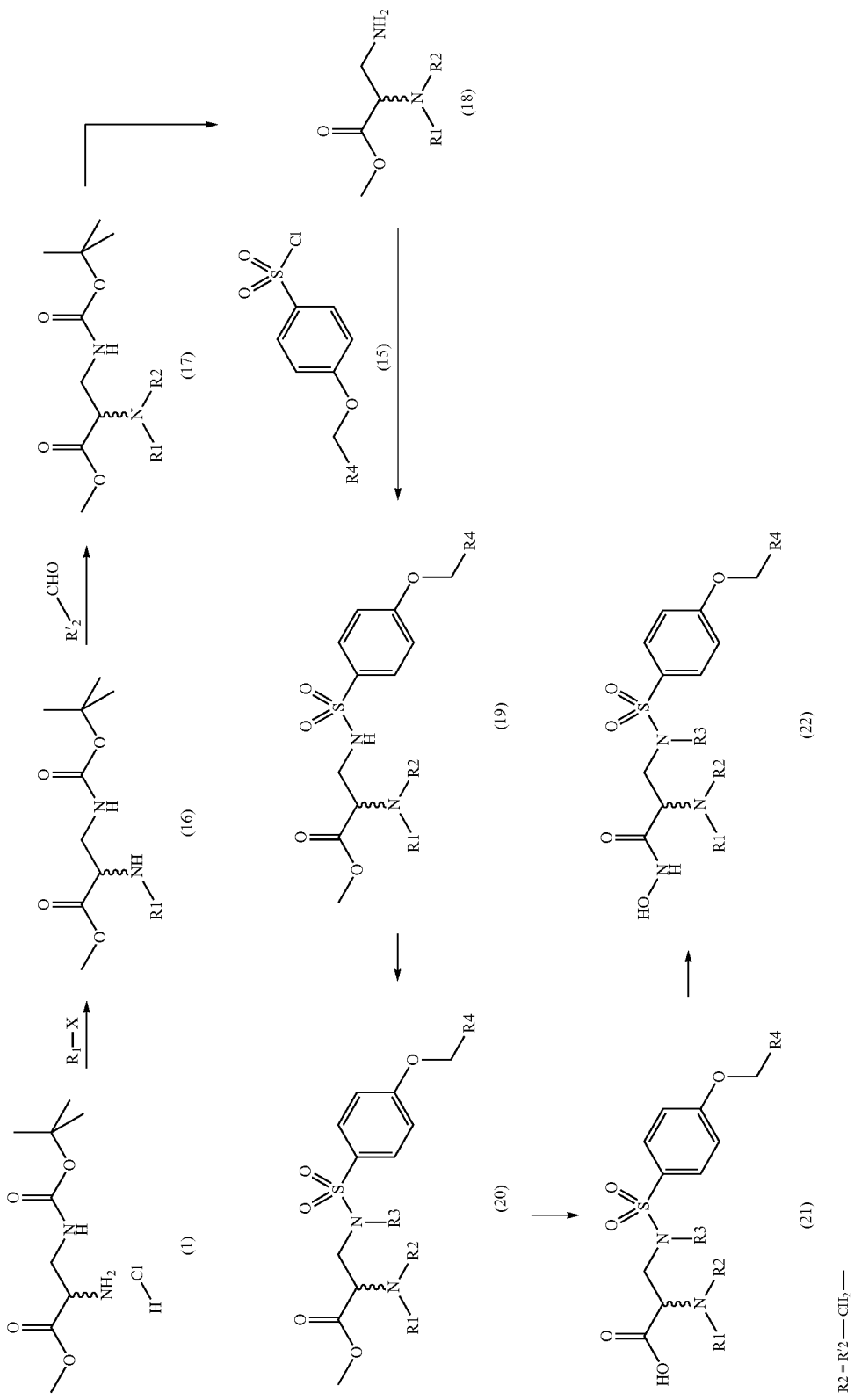

The compounds of general formula (I) in which R1 and R2, which may be identical or different, are alkyl radicals, are prepared according to the reaction scheme of figure 3 presented below.

According to figure 3, the compounds (16) are obtained by reaction between the amino acid (1) H-DAP(Boc)-OMe.HCl or H-(D)-DAP(Boc)-OMe.HCl and an alkyl halide $R_1$—X in the presence of an organic tertiary base such as diisopropylethylamine or triethylamine at a temperature of between 60° C. and 120° C. A reductive amination with an aliphatic aldehyde $R'_2$—CHO in the presence of sodium cyanoborohydride, for example, makes it possible to obtain the derivative (17). After deprotection of the amine function, the compound (18) is obtained. It is then condensed with the sulfonyl chloride (15) so as to give the derivative (19). In the case where R3 is a lower alkyl radical, an N-alkylation of the sulfonamide function is then carried out by reaction with an alkyl halide $R_3$—X in the presence of a base such as, for example, potassium carbonate in a solvent such as DMF, so as to give the derivative (20). The compound (21) is obtained via a saponification reaction in the presence of a base such as lithium hydroxide in the presence of water and of tetrahydrofuran for example. In a final step, the compound (22) is obtained by coupling between O-(tert-butyldimethylsilyl)hydroxylamine for example and the derivative (21) under conventional peptide coupling conditions, using, for example, 1-(3-dimethylaminopropyl)-3-ethylcarbodiimide hydrochloride, hydroxybenzotriazole or TBTU as coupling agents, and triethylamine or diisopropylethylamine as base, in a solvent such as dichloromethane or dimethylformamide. The deprotection of the silylated hydroxamic acid intermediately formed is carried out in situ or by washing with an acidic aqueous solution, so as to give the compound (22).

According to the present invention, the preferred compounds of general formula (I) are those for which:

$R_1$ and $R_2$, which may be identical or different, represent alkyl radicals or else they form a ring with the nitrogen atom to which they are attached, said ring being represented by the formula below:

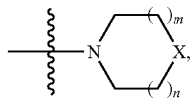

X, m and n having the meanings given hereinafter;
$R_3$ is a hydrogen atom or a a lower alkyl radical;
$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
X represents an oxygen atom, a —$CH_2$— radical, a —CH—($CH_2$)p-$NR_5R_6$ radical, a sulfur atom, an SO radical or an $SO_2$ radical, $R_5$, $R_6$ and p having the meanings given hereinafter;
$R_5$ and $R_6$, which may be identical or different, represent a hydrogen atom, an alkyl radical, a substituted alkyl radical, an aryl radical or a substituted aryl radical;
m can take the values of 0 or 1;
n can take the values of 0, 1 or 2;
p can take the values of 0, 1 or 2;
and also their addition salts with a pharmaceutically acceptable acid, their addition salts with a pharmaceutically acceptable base, and the enantiomers of said compounds.

According to the present invention, the particularly preferred compounds of general formula (I) are those for which:
$R_1$ and $R_2$ are identical or different and represent alkyl radicals or else they form a ring with the nitrogen atom to which they are attached, said ring being represented by the formula below:

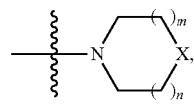

X, m and n having the meanings given hereinafter;
$R_3$ is a hydrogen atom or a a lower alkyl radical;
$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
X represents an oxygen atom, a —$CH_2$— radical or a —CH—($CH_2$)p-$NR_5R_6$ radical, $R_5$, $R_6$ and p having the meanings given hereinafter;
$R_5$ and $R_6$, which may be identical or different, represent a hydrogen atom, an alkyl radical, a substituted alkyl radical, an aryl radical or a substituted aryl radical;
m takes the value of 1;
n can take the values of 0, 1 or 2;
p can take the values of 0, 1 or 2;
and also their addition salts with a pharmaceutically acceptable acid, their addition salts with a pharmaceutically acceptable base, and the enantiomers of said compounds.

According to the present invention, the more particularly preferred compounds of general formula (I) are those for which:
$R_1$ and $R_2$ are identical or different and form a ring with the nitrogen atom to which they are attached, said ring being represented by the formula below:

X, m and n having the meanings given hereinafter;
$R_3$ is a hydrogen atom;
$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;
X represents an oxygen atom, a —$CH_2$ radical or a —CH—($CH_2$)p-$NR_5R_6$ radical, $R_5$, $R_6$ and p having the meanings given hereinafter;
$R_5$ and $R_6$, which may be identical or different, represent a hydrogen atom, an alkyl radical, a substituted alkyl radical, an aryl radical or a substituted aryl radical;
m takes the value of 1;
n can take the values of 1 or 2;
p can take the values of 0, 1 or 2;
and also their addition salts with a pharmaceutically acceptable acid, their addition salts with a pharmaceutically acceptable base, and the enantiomers of said compounds.

According to the present invention, the even more particularly preferred compounds of general formula (I) are those for which:
$R_1$ and $R_2$ are identical or different and form a ring with the nitrogen atom to which they are attached, said ring being represented by the formula below:

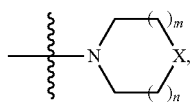

X, m and n having the meanings given hereinafter;
R₃ is a hydrogen atom;
R₄ is a heterocyclic radical, a substituted heterocyclic radical, a heteroaryl radical, a substituted heteroaryl radical, a heteroaralkyl radical or a substituted heteroaralkyl radical;
X represents an oxygen atom or a —CH₂ radical;
m takes the value of 1;
n takes the value of 1;
and also their addition salts with a pharmaceutically acceptable acid, their addition salts with a pharmaceutically acceptable base, and the enantiomers of said compounds.

According to the present invention, the most particularly preferred compounds of general formula (I) are those for which:
R₁ and R₂ are identical or different and form a ring with the nitrogen atom to which they are attached, said ring being represented by the formula below:

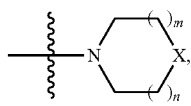

X, m and n having the meanings given hereinafter;
R₃ is a hydrogen atom;
R₄ is a heteroaryl radical or a substituted heteroaryl radical;
X represents an oxygen atom or a —CH₂ radical;
m takes the value of 1;
n takes the value of 1;
and also their addition salts with a pharmaceutically acceptable acid, their addition salts with a pharmaceutically acceptable base, and the enantiomers of said compounds.

The compounds according to the invention exhibit a very good TACE-inhibiting activity and, in particular, they inhibit the TACE enzyme selectively compared with other ADAMs and MMPs. This TACE enzyme-inhibiting activity is measured in an enzymatic assay and quantified by measuring an IC₅₀ (inhibitory concentration necessary for obtaining 50% inhibition of the TACE enzyme), as described in example 17. The compounds of the present invention have an IC₅₀ for TACE less than or equal to 10 μM and more particularly less than or equal to 1 μM. Advantageously, the compounds of the present invention have an IC₅₀ for TACE less than or equal to 0.5 μM.

Advantageously, these compounds are also very selective for TACE compared with the other ADAMs and MMPs (see example 18): their inhibitory activity is at least 10 times greater for TACE than for other ADAMs and MMPs (i.e. the IC₅₀ value for TACE is at least 10 times lower than that for other ADAMs and MMPs), and more advantageously at least 100 times greater.

TACE (TNFα-converting enzyme) catalyses the formation of soluble TNF-alpha from the precursor protein (transmembrane TNFα) bound to the membranes of certain cells. TNFα is a pro-inflammatory cytokine which is known to play a role in many pathological conditions with an inflammatory nature.

The invention is therefore directed toward the use of at least one compound of general formula (I) as defined above, for the treatment of pathological conditions or disorders linked to TNFα release. A TACE enzyme inhibitor of general formula (I) decreases TNFα production. As a result, it is of use for the treatment of pathological conditions linked to TNFα release.

The invention is also directed toward the use of at least one compound of general formula (I) as defined above, for preparing a pharmaceutical or cosmetic composition in which said compound has TACE enzyme-inhibiting activity.

It is therefore directed toward the use of at least one compound of general formula (I) as defined above, for the treatment of pathological conditions or disorders which are improved by inhibiting the TACE enzyme.

The invention also relates to a method of therapeutic (human or animal) or cosmetic treatment, which consists of the administration or the application of a pharmaceutical or cosmetic composition comprising a compound of general formula (I) as a TACE inhibitor and, consequently, as an inhibitor of soluble TNFα production.

Thus, the invention relates to the use of at least one compound of general formula (I) as defined above, for the treatment of pathological conditions or disorders linked to TNFα production.

The invention also relates to the use of a compound of general formula (I) as defined above, for preparing a medicament intended for the treatment of pathological conditions for which reducing TNFα production would be of great interest.

Indeed, the compounds used according to the invention are particularly suitable for the treatment and prevention of disorders/diseases such as the inflammatory diseases listed hereinafter, but are not limited thereto, such as septic shock, hemodynamic shock, malaria, inflammatory bowel diseases (IBDs) such as Crohn's disease and ulcerative colitis, inflammatory bone diseases, mycobacterial infections, meningitis, fibrotic diseases, cardiac diseases, atherosclerosis, obesity, ischemic attack, transplant rejection, cancer, diseases involving angiogenesis phenomena, autoimmune diseases, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), inflammatory skin diseases, psoriasis, atopic dermatitis and psoriatic arthritis.

These molecules are also potential active ingredients for the treatment of neurological pathological conditions with an inflammatory nature, for which reducing TNFα production would be of great interest. These pathological conditions listed hereinafter in a nonlimiting manner are, for example, Alzheimer's disease, Parkinson's disease, parkinsonian disorders, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barre syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease and stroke.

The invention relates to the use of a compound of general formula (I) as defined above, for preparing a medicament intended for the treatment of pathological conditions with an inflammatory nature, in which TNFα is involved.

The invention also relates to the use of a compound of general formula (I) as defined above, for preparing a medicament intended for the treatment of inflammatory skin diseases, for the treatment of psoriasis, atopic dermatitis or psoriatic arthritis.

A subject of the present invention is also a pharmaceutical composition intended in particular for the treatment of the abovementioned conditions, and which is characterized in that it comprises, in a carrier which is pharmaceutically acceptable and compatible with the method of administration selected for this composition, at least one compound of general formula (I). This compound of general formula (I) can also be in one of its enantiomeric forms or in the form of one of its pharmaceutically acceptable salts.

Several examples of preparation of active compounds of formula (I) according to the invention, and also of the results of biological activity of such compounds, will now be given by way of illustration and without being in any way limiting in nature.

EXEMPLARY EMBODIMENTS

The compounds of general formula (I) are characterized by proton NMR analysis on a Bruker Avance 400 MHz instrument.

Example 1

(S)-3-(4-benzyloxybenzenesulfonylamino)-N-hydroxy-2-piperidin-1-ylpropionamide 1.1: Methyl(S)-3-tert-butoxycarbonylamino-2-piperidin-1-ylpropanoate 14.4 ml (104 mmol) of triethylamine are added to a solution of 8.0 g (31 mmol) of commercial methyl (S)-2-amino-3-tert-butoxycarbonylaminopropanoate hydrochloride in 160 ml of tert-butanol, and then the reaction medium is stirred for 30 min at 40° C., and filtered in order to remove the triethylammonium salts. 6 ml (44 mmol) of 1,5-dibromopentane are added to the filtrate thus obtained, and the reaction medium is heated at 80° C. for 3 days. After the insoluble material has been filtered off, the filtrate is concentrated under vacuum. The crude residue is purified by chromatography on silica gel, elution being carried out with a 70/30 heptane/ethyl acetate mixture. 5.3 g (59%) of methyl(S)-3-tert-butoxycarbonylamino-2-piperidin-1-ylpropanoate are obtained in the form of a colorless oil.

1.2: Methyl(S)-3-amino-2-piperidin-1-ylpropanoate dihydrochloride

A solution of 750 mg (2.6 mmol) of methyl(S)-3-tert-butoxycarbonylamino-2-piperidin-1-ylpropanoate in 6 ml of methanol and 6 ml of isopropanolic hydrochloric acid, having a concentration of 5-6N, is stirred at 40° C. for 18 h. After concentration under vacuum, the residue is taken up in ethyl acetate, filtered and dried under vacuum. 670 mg (98%) of methyl(S)-3-amino-2-piperidin-1-ylpropanoate dihydrochloride are obtained in the form of a white solid.

1.3: Sodium salt of 4-benzyloxybenzenesulfonic acid 64 ml (539 mmol) of benzyl bromide are added to a solution of 50 g (215 mmol) of the sodium salt of 4-hydroxybenzenesulfonic acid dihydrate in 700 ml of isopropanol and 250 ml (250 mmol) of an aqueous solution of sodium hydroxide having a concentration of 1M. The reaction medium is heated at 70° C. for 20 h. After concentration of the isopropanol under vacuum, the product precipitates and is filtered off. 61 g (100%) of the sodium salt of 4-benzyloxybenzenesulfonic acid are obtained in the form of a white solid.

1.4: 4-Benzyloxybenzenesulfonyl chloride

A solution of 55 ml (639 mmol) of oxalyl chloride in 250 ml of dichloromethane is added dropwise to a solution of 61 g (213 mmol) of the sodium salt of 4-benzyloxybenzenesulfonic acid in 200 ml of dimethylformamide, while maintaining the temperature between −20° C. and −10° C. After addition, the reaction medium is slowly brought back to ambient temperature and then stirred for 18 h, poured onto ice and extracted with ethyl acetate. The organic phase is washed with water and with a saturated aqueous solution of sodium chloride and concentrated under vacuum. 54 g (89%) of 4-benzyloxybenzenesulfonyl chloride are obtained in the form of a white solid.

1.5: Methyl(S)-3-(4-benzyloxybenzenesulfonylamino)-2-piperidin-1-ylpropanoate 1.2 ml (8.5 mmol) of triethylamine and then 800 mg (2.8 mmol) of 4-benzyloxybenzenesulfonyl chloride in 8 ml of dichloromethane are added to a solution of 670 mg (2.6 mmol) of methyl(S)-3-amino-2-piperidin-1-ylpropanoate in 10 ml of dichloromethane. The reaction medium is stirred at ambient temperature for 18 h, hydrolyzed and then diluted with dichloromethane. The product is extracted with dichloromethane. The organic phase is washed with water and then with a saturated aqueous solution of sodium chloride, dried over magnesium sulfate, filtered and concentrated under vacuum. The residue obtained is purified by chromatography on silica gel, elution being carried out with a 70/30 heptane/ethyl acetate mixture. 940 mg (85%) of methyl(S)-3-(4-benzyloxybenzenesulfonylamino)-2-piperidin-1-ylpropanoate are obtained in the form of a white solid.

1.6: (S)-3-(4-benzyloxybenzenesulfonylamino)-2-piperidin-1-ylpropanoic acid 1.6 ml (1.6 mmol) of an aqueous solution of lithium hydroxide having a concentration of 1N are added to a solution of 450 mg (1.1 mmol) of methyl(S)-3-(4-benzyloxybenzenesulfonylamino)-2-piperidin-1-ylpropanoate in 15 ml of tetrahydrofuran and 0.5 ml of water. After stirring at ambient temperature for 18 h, the tetrahydrofuran is evaporated off under vacuum and then 1.8 ml of an aqueous solution of acetic acid having a concentration of 1N and 15 ml of water are added. The product precipitates and is filtered off. 420 mg (98%) of (S)-3-(4-benzyloxybenzenesulfonylamino)-2-piperidin-1-ylpropanoic acid are obtained in the form of a white solid.

1.7: (S)-3-(4-benzyloxybenzenesulfonylamino)-N-hydroxy-2-piperidin-1-ylpropionamide 150 mg (1.1 mmol) of 1-hydroxybenzotriazole and 210 mg (1.1 mmol) of 1-ethyl-3-(3-dimethyl-aminopropyl)carbodiimide hydrochloride are added to a solution of 420 mg (1.0 mmol) of (S)-3-(4-benzyloxybenzenesulfonylamino)-2-piperidin-1-ylpropanoic acid in 15 ml of dimethylformamide. The reaction medium is stirred for 20 min and then a solution of 160 mg (1.1 mmol) of O-tert-butyldimethylsilylhydroxylamine in 3 ml of dimethylformamide is added. The reaction medium is then stirred at ambient temperature for 18 h and then hydrolyzed with 2 ml of a saturated aqueous solution of sodium hydrogen carbonate and 2 ml of water. After stirring for 20 min in order to complete the deprotection of the hydroxamate, the product is extracted with ethyl acetate. The organic phases are washed with a saturated aqueous solution of sodium hydrogen carbonate and then with a saturated aqueous solution of sodium chloride, dried over magnesium sulfate, filtered and concentrated under vacuum. The residue obtained is crystallized from isopropyl ether under hot conditions, and then filtered off. The resulting solid is recrystallized from a 1/1 heptane/ethyl acetate mixture, filtered and then oven-dried under vacuum for 4 h. 150 mg of (S)-3-(4-benzyloxybenzenesulfonylamino)-N-hydroxy-2-piperidin-1-ylpropionamide are obtained in the form of a beige solid with a melting point of 126° C.

$^1$H NMR (δ, DMSO): 1.24-1.34 (m, 2H); 1.34-1.40 (m, 4H); 2.33-2.37 (m, 4H); 2.70-2.79 (t, J=10.8 Hz, 1H); 2.95-2.99 (m, 2H); 5.19 (s, 2H); 7.19 (d, J=8 Hz, 2H); 7.32 (m, 1H); 7.33-7.48 (m, 5H); 7.74 (d, J=8 Hz, 2H); 8.86 (s, 1H); 10.53 (s, 1H).

Example 2

(S)-3-(4-benzyloxybenzenesulfonylamino)-N-hydroxy-2-pyrrolidin-1-ylpropionamide 2.1: Methyl(S)-3-tert-butoxycarbonylamino-2-pyrrolidin-1-ylpropanoate 10 ml (65 mmol) of triethylamine are added to a solution of 5 g (20 mmol) of commercial methyl(S)-2-amino-3-tert-butoxycarbonylaminopropanoate hydrochloride in 150 ml of tert-butanol. The reaction medium is stirred for 20 min at 40° C. and then filtered in order to remove the triethylammonium salts. 3.8 ml (32 mmol) of 1,4-dibromobutane are added to the filtrate thus obtained, and the reaction medium is heated at 80° C. for 3 days. After the insoluble material has been filtered off, the filtrate is concentrated under vacuum. The residue obtained is purified by chromatography on a silica column, elution being carried out with a 98/2 dichloromethane/methanol mixture. 2.9 g (55%) of methyl(S)-3-tert-butoxycarbonylamino-2-pyrrolidin-1-ylpropanoate are obtained in the form of a yellow oil.

2.2: Methyl(S)-3-amino-2-pyrrolidin-1-ylpropanoate dihydrochloride

A solution of 2.9 g (11 mmol) of methyl(S)-3-tert-butoxycarbonylamino-2-pyrrolidin-1-ylpropanoate in 20 ml of isopropanolic hydrochloric acid having a concentration of 5-6N is stirred at 40° C. for 18 h. After evaporation under vacuum, the residue is taken up in 100 ml of diethyl ether, stirred at ambient temperature for 1 h, filtered and dried under vacuum. 2.3 g (88%) of methyl(S)-3-amino-2-pyrrolidin-1-ylpropanoate dihydrochloride are obtained in the form of a beige solid.

2.3: Methyl(S)-3-(4-benzyloxybenzenesulfonylamino)-2-pyrrolidin-1-ylpropanoate

In a manner analogous to example 1.5, using 2.3 g (9 mmol) of methyl(S)-3-amino-2-pyrrolidin-1-ylpropanoate dihydrochloride and 2.9 g (10 mmol) of 4-benzyloxybenzenesulfonyl chloride (prepared according to example 1.4), 3.5 g (90%) of methyl(S)-3-(4-benzyloxybenzenesulfonylamino)-2-pyrrolidin-1-ylpropanoate are obtained in the form of a white solid.

2.4: (S)-3-(4-benzyloxybenzenesulfonylamino)-2-pyrrolidin-1-ylpropanoic acid

In a manner analogous to example 1.6, using 500 mg (1.2 mmol) of methyl(S)-3-(4-benzyloxybenzenesulfonylamino)-2-pyrrolidin-1-ylpropanoate, 450 mg (94%) of (S)-3-(4-benzyloxybenzenesulfonylamino)-2-pyrrolidin-1-ylpropanoic acid are obtained in the form of a white solid.

2.5: (S)-3-(4-benzyloxybenzenesulfonylamino)-N-hydroxy-2-pyrrolidin-1-ylpropionamide In a manner analogous to example 1.7, using 450 mg (1.1 mmol) of (S)-3-(4-benzyloxybenzenesulfonylamino)-2-pyrrolidin-1-ylpropanoic acid, 150 mg (33%) of (S)-3-(4-benzyloxybenzenesulfonylamino)-N-hydroxy-2-pyrrolidin-1-ylpropionamide are obtained in the form of a white solid with a melting point of 186° C.

$^1$H NMR (δ, DMSO): 1.50-1.60 (m, 4H); 2.41-2.44 (m, 2H); 2.51-2.54 (m, 2H); 2.77-2.81 (m, 1H); 2.93-2.99 (m, 1H); 3.06 (t, J=6.4 Hz, 1H); 5.19 (s, 2H); 7.18 (d, J=8.9 Hz, 2I); 7.30-7.33 (m, 1H); 7.34-7.48 (m, 5H); 7.72 (d, J=8.9 Hz, 2H); 8.86 (s, 1H); 10.61 (s, 1H).

Example 3

(S)-3-[4-(4-fluorobenzyloxy)benzenesulfonylamino]-N-hydroxy-2-piperidin-1-yl-propionamide 3.1: Methyl(S)-3-(4-hydroxybenzenesulfonylamino)-2-piperidin-1-ylpropanoate A solution of 4.9 g (11 mmol) of methyl(S)-3-(4-benzyloxybenzenesulfonylamino)-2-piperidin-1-yl-propanoate (prepared as described in 1.5) in 80 ml of ethyl acetate, 30 ml of dioxane and 0.5 ml of glacial acetic acid is degassed under nitrogen for 15 min and then a suspension of 490 mg (10% by weight) of palladium on carbon at 10% in 3 ml of dioxane is added. The reaction medium is then placed under a hydrogen atmosphere and stirred at ambient temperature for 5 h. After filtration through celite, the filtrate is concentrated under vacuum. The residue is taken up in ethyl acetate, washed with water, dried over magnesium sulfate, filtered and concentrated. 3.8 g (97%) of methyl (S)-3-(4-hydroxybenzenesulfonylamino)-2-piperidin-1-ylpropanoate are obtained in the form of a white solid.

3.2: Methyl(S)-3-[4-(4-fluorobenzyloxy)benzenesulfonylamino]-2-piperidin-1-ylpropanoate 420 mg (1.3 mmol) of cesium carbonate and then 0.2 ml (1.3 mmol) of 1-bromomethyl-4-fluorobenzene are added to a solution of 400 mg (1.2 mmol) of methyl(S)-3-(4-hydroxybenzenesulfonylamino)-2-piperidin-1-ylpropanoate in 10 ml of acetone. After stirring at ambient temperature for 18 h, the reaction medium is filtered and then the filtrate is concentrated under vacuum. The crude product is purified by chromatography on silica gel, elution being carried out with a 70/30 heptane/ethyl acetate mixture. 460 mg (87%) of methyl (S)-3-[4-(4-fluorobenzyloxy)benzenesulfonylamino]-2-piperidin-1-ylpropanoate are obtained in the form of a white solid.

3.3: (S)-3-[4-(4-fluorobenzyloxy)benzenesulfonylamino]-2-piperidin-1-ylpropanoic acid In a manner analogous to example 1.6, using 460 mg (1.0 mmol) of methyl(S)-3-[4-(4-fluorobenzyloxy)benzenesulfonylamino]-2-piperidin-1-ylpropanoate, 380 mg (86%) of (S)-3-[4-(4-fluorobenzyloxy)benzenesulfonylamino]-2-piperidin-1-ylpropanoic acid are obtained in the form of a white solid.

3.4 (S)-3-[4-(4-fluorobenzyloxy)benzenesulfonylamino]-N-hydroxy-2-piperidin-1-ylpropionamide In a manner analogous to example 1.7, using 380 mg (0.9 mmol) of (S)-3-[4-(4-fluorobenzyloxy)-benzenesulfonylamino]-2-piperidin-1-ylpropanoic acid, 170 mg (43%) of (S)-3-[4-(4-fluorobenzyloxy)-benzenesulfonylamino]-N-hydroxy-2-piperidin-1-ylpropionamide are obtained in the form of a white solid with a melting point of 140° C.

$^1$H NMR (δ, DMSO): 1.30-1.34 (m, 2H); 1.35-1.40 (m, 4H); 2.29-2.37 (m, 4H); 2.77-2.79 (m, 1H); 2.95-2.99 (m, 2H); 5.18 (s, 2H); 7.18-7.27 (m, 4H); 7.34 (s, 1H); 7.50-7.54 (m, 2H); 7.72-7.75 (m, 2H); 8.85 (s, 1H); 10.53 (s, 1H).

Example 4

(S)-3-[(4-benzyloxybenzenesulfonyl)methylamino]-N-hydroxy-2-piperidin-1-yl-propionamide

4.1: Methyl(S)-3-[(4-benzyloxybenzenesulfonyl)methylamino]-2-piperidin-1-ylpropanoate 190 mg (1.4 mmol) of potassium carbonate and then 0.15 ml (2.3 mmol) of methyl iodide are added to a solution of 500 mg (1.2 mmol) of methyl(S)-3-(4-benzyloxybenzenesulfonylamino)-2-piperidin-1-yl-propanoate (prepared as described in 1.5) in 10 ml of dimethylformamide. The reaction medium is then stirred at ambient temperature for 18 h, filtered and then concentrated under vacuum. The crude residue is purified by chromatography on silica gel, elution being carried out with an 8/2 heptane/ethyl acetate mixture. 400 mg (78%) of methyl(S)-3-[(4-benzyloxybenzenesulfonyl)methylamino]-2-piperidin-1-ylpropanoate are obtained in the form of a colorless oil.

4.2: (S)-3-[(4-benzyloxybenzenesulfonyl)methylamino]-2-piperidin-1-ylpropanoic acid In a manner analogous to example 1.6, using 400 mg (0.9 mmol) of methyl(S)-3-[(4-benzyloxybenzenesulfonyl)methylamino]-2-piperidin-1-ylpropanoate, 350 mg (92%) of (S)-3-[(4-benzyloxybenzenesulfonyl)methylamino]-2-piperidin-1-ylpropanoic acid are obtained in the form of a white solid.

4.3: (S)-3-[(4-benzyloxybenzenesulfonyl)methylamino]-N-hydroxy-2-piperidin-1-ylpropionamide In a manner analogous to example 1.7, using 350 mg (0.8 mmol) of (S)-3-[(4-benzyloxybenzenesulfonyl)methylamino]-2-piperidin-1-ylpropanoic acid, 30 mg (8%) of (S)-3-[(4-benzyloxybenzenesulfonyl)methylamino]-N-hydroxy-2-piperidin-1-ylpropionamide are obtained in the form of a cream solid with a melting point of 102° C.

$^1$H NMR (δ, DMSO): 1.33-1.34 (m, 2H); 1.41-1.43 (m, 4H); 2.41-2.43 (m, 2H); 2.52-2.54 (m, 2H); 2.65 (s, 3H); 3.02-3.09 (m, 1H); 3.13-3.19 (m, 2H); 5.21 (s, 2H); 7.23 (d, J=8.8 Hz, 2H); 7.34-7.43 (m, 3H); 7.47 (d, J=7 Hz, 2H); 7.71 (d, J=8.8 Hz, 2H); 8.91 (s, 1H); 10.59 (s, 1H).

Example 5

(S)—N-Hydroxy-3-[4-(naphthalen-2-ylmethoxy)benzenesulfonylamino]-2-piperidin-1-ylpropionamide

5.1: Methyl(S)-3-[4-(naphthalen-2-ylmethoxy)benzenesulfonylamino]-2-piperidin-1-ylpropanoate 420 mg (1.3 mmol) of cesium carbonate, followed by 280 mg (1.3 mmol) of 2-bromomethylnaphthalene, are added to a solution of 400 mg (1.2 mmol) of methyl(S)-3-(4-hydroxy-benzenesulfonylamino)-2-piperidin-1-ylpropanoate (prepared as described in 3.1) in 10 ml of acetone. The reaction medium is stirred at ambient temperature for 18 h and then filtered. The filtrate is concentrated under vacuum and purified by chromatography on silica gel, elution being carried out with a 70/30 heptane/ethyl acetate mixture. 420 mg (80%) of methyl(S)-3-[4-(naphthalen-2-ylmethoxy)benzenesulfonylamino]-2-piperidin-1-ylpropanoate are obtained in the form of a white solid.

5.2: (S)-3-[4-(Naphthalen-2-ylmethoxy)benzenesulfonylamino]-2-piperidin-1-ylpropanoic acid In a manner analogous to example 1.6, using 420 mg (0.9 mmol) of methyl(S)-3-[4-(naphthalen-2-ylmethoxy)benzenesulfonylamino]-2-piperidin-1-ylpropanoate, 370 mg (90%) of (S)-3-[4-(naphthalen-2-ylmethoxy)benzenesulfonylamino]-2-piperidin-1-ylpropanoic acid are obtained in the form of a white solid.

5.3: (S)—N-hydroxy-3-[4-(naphthalen-2-ylmethoxy)benzenesulfonylamino]-2-piperidin-1-ylpropionamide In a manner analogous to example 1.7, using 370 mg (0.8 mmol) of (S)-3-[4-(naphthalen-2-ylmethoxy)benzenesulfonylamino]-2-piperidin-1-ylpropanoic acid, 30 mg (8%) of (S)—N-hydroxy-3-[4-(naphthalen-2-ylmethoxy)benzenesulfonylamino]-2-piperidin-1-ylpropionamide are obtained in the form of a beige solid with a melting point of 106° C.

$^1$H NMR (δ, DMSO): 1.28-1.30 (m, 2H); 1.35-1.45 (m, 4H); 2.30-2.40 (m, 4H); 2.76-2.81 (m, 1H); 2.95-2.97 (m, 1H); 2.97-3.01 (1H); 5.38 (s, 2H); 7.24 (d, J=8.9 Hz, 2H); 7.33 (m, 1H); 7.53-7.56 (m, 2H); 7.59 (d, J=8.4 Hz, 1H); 7.75 (d, J=8.8 Hz, 2H); 7.93-7.97 (m, 3H); 8.01 (s, 1H); 8.85 (s, 1H); 10.53 (s, 1H).

Example 6

(S)-3-[4-(3,4-dichlorobenzyloxy)benzenesulfonylamino]-N-hydroxy-2-piperidin-1-yl-propionamide

6.1: Methyl(S)-3-[4-(3,4-dichlorobenzyloxy)benzenesulfonylamino]-2-piperidin-1-ylpropanoate In a manner analogous to example 5.1, using 310 mg (1.3 mmol) of 4-bromomethyl-1,2-dichlorobenzene and 400 mg (1.2 mmol) of methyl(S)-3-(4-hydroxybenzenesulfonylamino)-2-piperidin-1-yl-propanoate (prepared as described in 3.1), 460 mg (78%) of methyl(S)-3-[4-(3,4-dichlorobenzyloxy)-benzenesulfonylamino]-2-piperidin-1-ylpropanoate are obtained in the form of a white solid.

6.2: (S)-3-[4-(3,4-dichlorobenzyloxy)benzenesulfonylamino]-2-piperidin-1-ylpropanoic acid In a manner analogous to example 1.6, using 460 mg (0.9 mmol) of methyl(S)-3-[4-(3,4-dichloro-benzyloxy)benzenesulfonylamino]-2-piperidin-1-ylpropanoate, 420 mg (93%) of (S)-3-[4-(3,4-dichloro-benzyloxy)benzenesulfonylamino]-2-piperidin-1-ylpropanoic acid are obtained in the form of a white solid.

6.3: (S)-3-[4-(3,4-dichlorobenzyloxy)benzenesulfonylamino]-N-hydroxy-2-piperidin-1-ylpropionamide In a manner analogous to example 1.7, using 420 mg (0.9 mmol) of (S)-3-[4-(3,4-dichlorobenzyloxy)-benzenesulfonylamino]-2-piperidin-1-ylpropanoic acid, 240 mg (47%) of (S)-3-[4-(3,4-dichlorobenzyloxy)benzenesulfonylamino]-N-hydroxy-2-piperidin-1-ylpropionamide are obtained in the form of a white solid with a melting point of 166° C.
$^1$H NMR (δ, DMSO): 1.18-1.23 (m, 2H); 1.23-1.32 (m, 4H); 2.20-2.35 (m, 4H); 2.66-2.72 (m, 1H); 2.87-2.89 (m, 2H); 5.68 (s, 2H); 7.12 (d, J=8.8 Hz, 2H); 7.27 (s, 1H); 7.39 (d, J=8.2 Hz, 1H); 7.60 (d, J=8.2 Hz, 1H); 7.67 (d, J=8.6 Hz, 3H); 8.78 (s, 1H); 10.46 (s, 1H).

Example 7

(S)-3-(4-benzyloxybenzenesulfonylamino)-N-hydroxy-2-morpholin-4-ylpropionamide

7.1: Methyl(S)-3-tert-butoxycarbonylamino-2-morpholin-4-ylpropanoate 2.8 g (20 mmol) of 1-chloro-2-(2-chloroethoxy)ethane are added to a solution of 5 g (20 mmol) of commercial methyl (S)-2-amino-3-tert-butoxycarbonylaminopropanoate in 65 ml of diisopropylethylamine. The reaction mixture is stirred at 127° C. for 18 h. After the addition of water, the reaction medium is extracted with ethyl acetate. The organic phases are combined, dried over sodium sulfate, filtered and evaporated. The residue obtained is purified by chromatography on silica gel, elution being carried out with a 70/30 heptane/ethyl acetate mixture. 1.4 g (24%) of methyl(S)-3-tert-butoxycarbonylamino-2-morpholin-4-ylpropanoate are obtained in the form of an oil.

7.2: Methyl(S)-3-amino-2-morpholin-4-ylpropanoate

A solution of 1.4 g (5 mmol) of methyl(S)-3-tert-butoxycarbonylamino-2-morpholin-4-ylpropanoate in 20 ml of methanol and 10 ml of a solution of hydrochloric acid having a 5-6N concentration in isopropanol is stirred at 40° C. for 20 h and then evaporated to dryness. 1.3 g (96%) of methyl(S)-3-amino-2-morpholin-4-ylpropanoate hydrochloride are obtained in the form of a solid.

7.3: Methyl(S)-3-(4-benzyloxybenzenesulfonylamino)-2-morpholin-4-ylpropanoate A solution of 1.5 g (5.3 mmol) of 4-benzyloxybenzenesulfonyl chloride (prepared according to example 1.4) in 20 ml of dichloromethane is added dropwise to a solution of 1.3 g (4.8 mmol) of methyl(S)-3-amino-2-morpholin-4-ylpropanoate dihydrochloride and 2.7 ml (19.3 mmol) of triethylamine in 40 ml of dichloromethane. The reaction mixture is stirred at ambient temperature for 18 h. After the addition of water and extraction with dichloromethane, the organic phases are combined, dried over sodium sulfate and evaporated. The residue is purified by chromatography on silica gel, elution being carried out with a 60/40 heptane/ethyl acetate mixture.
1.8 g (87%) of methyl(S)-3-(4-benzyloxybenzenesulfonylamino)-2-morpholin-4-ylpropanoate are obtained in the form of a white solid.

7.4: (S)-3-(4-benzyloxybenzenesulfonylamino)-2-morpholin-4-ylpropanoic acid

In a manner analogous to example 1.6, using 500 mg (1.2 mmol) of methyl(S)-3-(4-benzyloxybenzenesulfonylamino)-2-morpholin-4-ylpropanoate, 434 mg (90%) of (S)-3-(4-benzyloxybenzenesulfonylamino)-2-morpholin-4-ylpropanoic acid are obtained in the form of a white solid.

7.5: (S)-3-(4-benzyloxybenzenesulfonylamino)-N-hydroxy-2-morpholin-4-ylpropionamide In a manner analogous to example 1.7, using 429 mg (1.0 mmol) of (S)-3-(4-benzyloxybenzenesulfonylamino)-2-morpholin-4-ylpropanoic acid, 12 mg (11%) of (S)-3-(4-benzyloxybenzenesulfonylamino)-N-hydroxy-2-morpholin-4-ylpropionamide are obtained in the form of a beige powder with a melting point of 142° C.
$^1$H NMR (δ, DMSO): 2.35-2.45 (m, 4H); 2.79-2.86 (m, 1H); 2.93-3.01 (m, 2H); 3.40-3.55 (m, 4H); 5.20 (s, 2H); 7.19 (d, J=8.8 Hz, 2H); 7.34-7.48 (m, 6H); 7.74 (d, J=8.7 Hz, 2H); 8.92 (s, 1H); 10.63 (s, 1H).

Example 8

(S)—N-hydroxy-3-[4-(2-methylquinolin-4-ylmethoxy)benzenesulfonylamino]-2-piperidin-1-ylpropionamide

8.1: Methyl(S)-3-[4-(2-methylquinolin-4-ylmethoxy)benzenesulfonylamino]-2-piperidin-1-ylpropanoate In a manner analogous to example 5.1, using 240 mg (1.3 mmol) of 4-chloromethyl-2-methylquinoline and 400 mg (1.2 mmol) of methyl(S)-3-(4-hydroxybenzenesulfonylamino)-2-piperidin-1-ylpropanoate (prepared as described in 3.1), 450 mg (77%) of methyl(S)-3-[4-(2-methylquinolin-4-ylmethoxy)-benzenesulfonylamino]-2-piperidin-1-ylpropanoate are obtained in the form of a white solid.

8.2: (S)-3-[4-(2-methylquinolin-4-ylmethoxy)benzenesulfonylamino]-2-piperidin-1-ylpropanoic acid In a manner analogous to example 1.6, using 450 mg (0.9 mmol) of methyl(S)-3-[4-(2-methylquinolin-4-ylmethoxy)benzenesulfonylamino]-2-piperidin-1-ylpropanoate, 360 mg (84%) of (S)-3-[4-(2-methylquinolin-4-ylmethoxy)benzenesulfonylamino]-2-piperidin-1-ylpropanoic acid are obtained in the form of a white solid.

8.3: (S)—N-hydroxy-3-[4-(2-methylquinolin-4-ylmethoxy)benzenesulfonylamino]-2-piperidin-1-ylpropionamide In a manner analogous to example 1.7, using 360 mg (0.7 mmol) of (S)-3-[4-(2-methylquinolin-4-ylmethoxy)benzenesulfonylamino]-2-piperidin-1-ylpropanoic acid, 50 mg (13%) of (S)—N-hydroxy-3-[4-(2-methylquinolin-4-ylmethoxy)benzenesulfonylamino]-2-piperidin-1-ylpropionamide are obtained in the form of a white solid with a melting point of 150° C.

$^1$H NMR (δ, DMSO): 1.29-1.31 (m, 2H); 1.39-1.40 (m, 4H); 2.34-2.38 (m, 4H); 2.67 (s, 3H); 2.73-2.79 (m, 1H); 2.96-2.99 (m, 2H); 5.72 (s, 2H); 7.33-7.37 (m, 3H); 7.57-7.62 (m, 2H); 7.74-7.80 (m, 1H); 7.98 (d, J=8.4 Hz, 2H); 8.11 (d, J=8.4 Hz, 2H); 8.86 (s, 1H), 10.54 (s, 1H).

Example 9

(S)-3-[4-(3,5-dichlorobenzyloxy)benzenesulfonylamino]-N-hydroxy-2-piperidin-1-yl-propionamide

9.1: Methyl(S)-3-[4-(3,5-dichlorobenzyloxy)benzenesulfonylamino]-2-piperidin-1-ylpropanoate In a manner analogous to example 5.1, using 240 mg (1.3 mmol) of 4-chloromethyl-2-methylquinoline and 400 mg (1.2 mmol) of methyl(S)-3-(4-hydroxybenzenesulfonylamino)-2-piperidin-1-ylpropanoate (prepared as described in 3.1), 400 mg (69%) of methyl(S)-3-[4-(3,5-dichlorobenzyloxy)-benzenesulfonylamino]-2-piperidin-1-ylpropanoate are obtained in the form of a white solid.

9.2: (S)-3-[4-(3,5-dichlorobenzyloxy)benzenesulfonylamino]-2-piperidin-1-ylpropanoic acid In a manner analogous to example 1.6, using 400 mg (0.8 mmol) of methyl(S)-3-[4-(3,5-dichlorobenzyloxy)benzenesulfonylamino]-2-piperidin-1-ylpropanoate, 360 mg (92%) of (S)-3-[4-(3,5-dichlorobenzyloxy)benzenesulfonylamino]-2-piperidin-1-ylpropanoic acid are obtained in the form of a white solid.

9.3: (S)-3-[4-(3,5-dichlorobenzyloxy)benzenesulfonylamino]-N-hydroxy-2-piperidin-1-ylpropionamide In a manner analogous to example 1.7, using 360 mg (0.7 mmol) of (S)-3-[4-(3,5-dichlorobenzyloxy)-benzenesulfonylamino]-2-piperidin-1-ylpropanoic acid, 80 mg (22%) of (S)-3-[4-(3,5-dichlorobenzyloxy)benzenesulfonylamino]-N-hydroxy-2-piperidin-1-ylpropionamide are obtained in the form of a yellow solid with a melting point of 130° C.

$^1$H NMR (δ, DMSO): 1.28-1.35 (m, 2H); 1.35-1.42 (m, 4H); 2.31-2.40 (m, 4H); 2.75-2.82 (m, 1H); 2.94-3.00 (m, 2H); 5.23 (s, 2H); 7.20 (d, J=8.9 Hz, 2H); 7.30-7.40 (m, 1H); 7.54 (s, 2H); 7.60 (s, 1H); 7.75 (d, J=8.5 Hz, 2H); 8.85 (s, 1H); 10.54 (s, 1H).

Example 10

(S)—N-hydroxy-2-piperidin-1-yl-3-(4-propoxybenzenesulfonylamino)propionamide

10.1: Methyl(S)-2-piperidin-1-yl-3-(4-propoxybenzenesulfonylamino)propanoate In a manner analogous to example 5.1, using 0.1 ml (1.5 mmol) of 1-bromopropane and 400 mg (1.2 mmol) of methyl (S)-3-(4-hydroxybenzenesulfonylamino)-2-piperidin-1-ylpropanoate (prepared as described in 3.1), 240 mg (53%) of methyl(S)-2-piperidin-1-yl-3-(4-propoxybenzenesulfonylamino)-propanoate are obtained in the form of a colorless oil.

10.2: (S)-2-piperidin-1-yl-3-(4-propoxybenzenesulfonylamino)propanoic acid

In a manner analogous to example 1.6, using 240 mg (0.6 mmol) of methyl(S)-2-piperidin-1-yl-3-(4-propoxybenzenesulfonylamino)propanoate, 180 mg (78%) of (S)-2-piperidin-1-yl-3-(4-propoxybenzenesulfonylamino)propanoic acid are obtained in the form of a white solid.

10.3: (S)—N-hydroxy-2-piperidin-1-yl-3-(4-propoxybenzenesulfonylamino)propionamide In a manner analogous to example 1.7, using 180 mg (0.5 mmol) of (S)-2-piperidin-1-yl-3-(4-propoxybenzenesulfonylamino)propanoic acid, 50 mg (27%) of (S)—N-hydroxy-2-piperidin-1-yl-3-(4-propoxybenzenesulfonylamino)propionamide are obtained in the form of a white solid with a melting point of 147° C.

$^1$H NMR (δ, DMSO): 0.91 (t, J=7.3 Hz, 3H); 1.20-1.26 (m, 2H); 1.30-1.40 (m, 4H); 1.63-1.72 (m, 2H); 2.25-2.35 (m, 4H); 2.65-2.75 (m, 1H); 2.85-2.95 (m, 2H); 3.94 (t, J=6.4 Hz, 2H); 7.02 (d, J=8.7 Hz, 2H); 7.25 (s, 1H); 7.65 (d, J=8.7 Hz, 2H); 8.78 (s, 1H); 10.42 (s, 1H).

Example 11

(S)-3-(4-cyclopropylmethoxybenzenesulfonylamino)-N-hydroxy-2-morpholin-4-yl-propionamide

11.1: Methyl(S)-3-(4-hydroxybenzenesulfonylamino)-2-morpholin-4-ylpropanoate 0.4 g of palladium on carbon at 10% is added to a solution of 4 g (9.2 mmol) of methyl(S)-3-(4-benzyloxybenzenesulfonylamino)-2-morpholin-4-ylpropanoate (prepared as described in example 7.3) in 200 ml of methanol and 20 ml of dioxane degassed beforehand with nitrogen. The reaction mixture is stirred for one hour at ambient temperature under atmospheric hydrogen pressure. After filtration through celite and concentration of the filtrate under vacuum, the residue obtained is purified by chromatography on silica gel, elution being carried out with a 60/40 ethyl acetate/heptane mixture. 2.6 g (81%) of methyl(S)-3-(4-hydroxybenzenesulfonylamino)-2-morpholin-4-ylpropanoate are obtained in the form of a white solid.

11.2: Methyl(S)-3-(4-cyclopropylmethoxybenzenesulfonylamino)-2-morpholin-4-ylpropanoate In a manner analogous to example 5.1, using 173 mg (1.3 mmol) of cyclopropylmethyl bromide and 400 mg (1.2 mmol) of methyl(S)-3-(4-hydroxybenzenesulfonylamino)-2-morpholin-4-ylpropanoate, 272 mg (59%) of methyl(S)-3-(4-cyclopropylmethoxybenzenesulfonylamino)-2-morpholin-4-yl-propanoate are obtained in the form of an oil.

11.3: (S)-3-(4-cyclopropylmethoxybenzenesulfonylamino)-2-morpholin-4-ylpropanoic acid In a manner analogous to example 1.6, using 262 mg (0.7 mmol) of methyl(S)-3-(4-cyclopropylmethoxybenzenesulfonylamino)-2-morpholin-4-ylpropanoate, 197 mg (78%) of (S)-3-(4-cyclopropylmethoxybenzenesulfonylamino)-2-morpholin-4-ylpropanoic acid are obtained in the form of a white powder.

11.4: (S)-3-(4-cyclopropylmethoxybenzene-sulfonylamino)-N-hydroxy-2-morpholin-4-ylpropionamide In a manner analogous to example 1.7, using 192 mg (0.5 mmol) of (S)-3-(4-cyclopropylmethoxybenzene-sulfonylamino)-2-morpholin-4-ylpropanoic acid, 88 mg (44%) of (S)-3-(4-cyclopropylmethoxybenzene-sulfonylamino)-N-hydroxy-2-morpholin-4-ylpropionamide are obtained in the form of a white powder with a melting point of 147° C.
$^1$H NMR (δ, DMSO): 0.82-0.90 (m, 2H); 0.58-0.68 (m, 2H); 1.25-1.35 (m, 1H); 2.43-2.41 (m, 4H); 2.80-2.90 (m, 1H); 2.90-2.98 (m, 1H); 2.98-3.05 (m, 1H); 3.48-3.58 (m, 4H); 3.94 (d, J=7 Hz, 2H); 7.13 (d, J=8.9 Hz, 2H); 7.47 (m, 1H); 7.75 (d, J=8.8 Hz, 2H); 8.95 (s, 1H); 10.67 (s, 1H).

Example 12

(S)-3-[4-(4-tert-butylbenzyloxy)benzenesulfonylamino]-N-hydroxy-2-morpholin-4-ylpropionamide

12.1: Methyl(S)-3-[4-(4-tert-butylbenzyloxy)benzenesulfonylamino]-2-morpholin-4-ylpropanoate In a manner analogous to example 5.1, using 290 mg (1.3 mmol) of 4-tert-butylbenzyl bromide and 400 mg (1.2 mmol) of methyl(S)-3-(4-hydroxybenzenesulfonylamino)-2-morpholin-4-ylpropanoate (prepared as described in example 11.1), 434 mg (76%) of methyl(S)-3-[4-(4-tert-butylbenzyloxy)-benzenesulfonylamino]-2-morpholin-4-ylpropanoate are obtained in the form of a white powder.

12.2: (S)-3-[4-(4-tert-butylbenzyloxy)benzenesulfonylamino]-2-morpholin-4-ylpropanoic acid In a manner analogous to example 1.6, using 429 mg (0.9 mmol) of methyl(S)-3-(4-cyclopropylmethoxybenzene-sulfonylamino)-2-morpholin-4-ylpropanoate, 359 mg (86%) of (S)-3-[4-(4-tert-butylbenzyloxy)benzenesulfonylamino]-2-morpholin-4-ylpropanoic acid are obtained in the form of a white powder.

12.3: (S)-3-[4-(4-tert-butylbenzyloxy)benzenesulfonylamino]-N-hydroxy-2-morpholin-4-ylpropionamide In a manner analogous to example 1.7, using 355 mg (0.8 mmol) of (S)-3-[4-(4-tert-butylbenzyloxy)-benzenesulfonylamino]-2-morpholin-4-ylpropanoic acid, 277 mg (76%) of (S)-3-[4-(4-tert-butylbenzyloxy)benzenesulfonylamino]-N-hydroxy-2-morpholin-4-ylpropionamide are obtained in the form of a beige powder with a melting point of 137° C.
$^1$H NMR (δ, DMSO): 1.28 (s, 9H); 2.40 (m, 4H); 2.79-2.83 (m, 1H); 2.93-3.01 (m, 2H); 3.46 (m, 4H); 5.15 (s, 2H); 7.18 (d, J=8.8 Hz, 2H); 7.40 (q, J=8.4 Hz, 5H); 7.74 (d, J=8.8 Hz, 2H); 8.92 (s, 1H); 10.63 (s, 1H).

Example 13

(S)—N-hydroxy-2-morpholin-4-yl-3-(4-phenethyloxybenzenesulfonylamino)-propionamide

13.1: Methyl(S)-2-morpholin-4-yl-3-(4-phenethyloxybenzenesulfonylamino)propanoate In a manner analogous to example 5.1, using 237 mg (1.3 mmol) of 2-bromoethylbenzene and 400 mg (1.2 mmol) of methyl(S)-3-(4-hydroxybenzenesulfonylamino)-2-morpholin-4-ylpropanoate (prepared as described in 11.1), 215 mg (41%) of methyl(S)-2-morpholin-4-yl-3-(4-phenethyloxybenzenesulfonylamino)propanoate are obtained in the form of a colorless oil.

13.2: (S)-2-morpholin-4-yl-3-(4-phenethyloxybenzenesulfonylamino)propanoic acid In a manner analogous to example 1.6, using 210 mg (0.5 mmol) of methyl(S)-2-morpholin-4-yl-3-[4-(pyridin-4-ylmethoxy)benzenesulfonylamino]propanoate, 155 mg (76%) of (S)-2-morpholin-4-yl-3-(4-phenethyloxybenzenesulfonylamino)propanoic acid are obtained in the form of a white powder.

13.3: (S)—N-hydroxy-2-morpholin-4-yl-3-(4-phenethyloxybenzenesulfonylamino)propionamide In a manner analogous to example 1.7, using 170 mg (0.4 mmol) of (S)-2-morpholin-4-yl-3-(4-phenethyloxybenzene-sulfonylamino)propanoic acid, 72 mg (46%) of (S)—N-hydroxy-2-morpholin-4-yl-3-(4-phenethyloxybenzenesulfonylamino)propionamide are obtained in the form of a beige powder with a melting point of 77° C.
$^1$H NMR (δ, DMSO): 2.35-2.42 (m, 4H); 2.75-2.85 (m, 1H); 2.90-3.01 (m, 2H); 3.06 (t, J=6.8 Hz, 2H); 3.40-3.50 (m, 4H); 4.28 (t, J=6.8 Hz, 2H); 7.11 (d, J=8.9 Hz, 2H); 7.25 (m, 1H); 7.32 (m, 4H); 7.45 (m, 1H); 7.71 (d, J=8.8 Hz, 2H); 8.91 (s, 1H); 10.62 (s, 1H).

Example 14

(S)—N-hydroxy-3-[4-(2-methylquinolin-4-ylmethoxy)benzenesulfonylamino]-2-morpholin-4-ylpropionamide

14.1: Methyl(S)-3-[4-(2-methylquinolin-4-ylmethoxy)benzenesulfonylamino]-2-morpholin-4-ylpropanoate In a manner analogous to example 5.1, using 245 mg (1.3 mmol) of 4-chloromethyl-2-methylquinoline and 400 mg (1.2 mmol) of methyl(S)-3-(4-hydroxybenzenesulfonylamino)-2-morpholin-4-ylpropanoate (prepared as described in example 11.1), 483 mg (83%) of methyl(S)-3-[4-(2-methylquinolin-4-ylmethoxy)benzenesulfonylamino]-2-morpholin-4-ylpropanoate are obtained in the form of a yellow oil.

14.2: (S)-3-[4-(2-methylquinolin-4-ylmethoxy)benzenesulfonylamino]-2-morpholin-4-ylpropanoic acid In a manner analogous to example 1.6, using 479 mg (1.0 mmol) of methyl(S)-3-[4-(2-methylquinolin-4-ylmethoxy)benzenesulfonylamino]-2-morpholin-4-ylpropanoate, 397 mg (85%) of (S)-3-[4-(2-methylquinolin-4-ylmethoxy)benzenesulfonylamino]-2-morpholin-4-ylpropanoic acid are obtained in the form of a beige powder.

14.3: (S)—N-hydroxy-3-[4-(2-methylquinolin-4-ylmethoxy)benzenesulfonylamino]-2-morpholin-4-yl-propionamide In a manner analogous to example 1.7, using 293 mg (0.5 mmol) of (S)-3-[4-(2-methylquinolin-4-ylmethoxy)benzenesulfonylamino]-2-morpholin-4-ylpropanoic acid, 121 mg (40%) of (S)—N-hydroxy-3-[4-(2-methylquinolin-4-ylmethoxy)benzenesulfonylamino]-2-morpholin-4-ylpropionamide are obtained in the form of a beige powder with a melting point of 138° C.

$^1$H NMR (δ, DMSO): 2.39-2.42 (m, 4H); 2.67 (s, 3H); 2.82-2.88 (m, 1H); 2.94-3.02 (m, 2H); 3.45-3.52 (m, 4H); 5.72 (s, 2H); 7.34 (d, J=8.9 Hz, 2H); 7.49 (m, 1H); 7.57-7.62 (m, 2H); 7.74-7.80 (m, 3H); 7.98 (d, J=8 Hz, 1H); 8.11 (d, J=7.8 Hz, 1H); 8.92 (s, 1H); 10.63 (s, 1H).

Example 15

(S)—N-hydroxy-3-[4-(2-methylquinolin-4-ylmethoxy)benzenesulfonylamino]-2-piperidin-1-ylpropionamide dihydrochloride 0.4 ml (2.0 mmol) of a solution of isopropanolic hydrochloric acid having a concentration of 5-6N is added to a solution of 400 mg (0.8 mmol) of (S)—N-hydroxy-3-[4-(2-methylquinolin-4-ylmethoxy)-benzenesulfonylamino]-2-piperidin-1-ylpropionamide (prepared as described in example 8) in 8 ml of isopropanol. The reaction medium is stirred at ambient temperature for 2 h and then filtered. The residue obtained is recrystallized from a 10/1 isopropanol/water mixture, filtered and dried under vacuum. 260 mg (56%) of (S)—N-hydroxy-3-[4-(2-methylquinolin-4-ylmethoxy)benzenesulfonylamino]-2-piperidin-1-ylpropionamide dihydrochloride are obtained in the form of a white solid with a melting point of 188° C.

$^1$H NMR (δ, DMSO): 1.30-1.40 (m, 1H); 1.60-1.80 (m, 4H); 1.85-1.95 (m, 1H); 2.85 (m, 1H); 3.00 (s, 3H); 3.10 (m, 1H); 3.25-3.35 (m, 3H); 3.45 (m, 1H); 3.80 (m, 1H); 5.98 (s, 2H); 7.45 (d, J=8.8 Hz, 2H); 7.85-7.94 (m, 3H); 8.05-8.10 (m, 1H); 8.10-8.15 (m, 2H); 8.44 (d, J=8 Hz, 2H), 11.03 (s, 1H), 11.54 (s, 1H).

Example 16

(R)—N-Hydroxy-3-[4-(2-methylquinolin-4-ylmethoxy)benzenesulfonylamino]-2-piperidin-1-ylpropionamide 16.1: Methyl (R)-3-tert-butoxycarbonylamino-2-piperidin-1-ylpropanoate 3.1 ml (20.6 mmol) of 1,5-diiodopentane are added to a solution of 5.0 g (19.6 mmol) of commercial methyl (R)-2-amino-3-tert-butoxycarbonylaminopropanoate hydrochloride and 0.22 g (0.6 mmol) of tetrabutylammonium chloride in 50 ml of N,N-diisopropylethylamine. The reaction medium is heated at 127° C. for 5 h and then at 100° C. for 18 h. After evaporation of a maximum amount of N,N diisopropylethylamine, the reaction medium is hydrolyzed and then diluted with ethyl acetate. The organic phase is washed with water, dried over magnesium sulfate, filtered and concentrated under vacuum.

The residue obtained is purified by chromatography on silica gel, elution being carried out with a 70/30 heptane/ethyl acetate mixture. 3.7 g (66%) of methyl (R)-3-tert-butoxycarbonylamino-2-piperidin-1-yl-propanoate are obtained in the form of a light oil.

16.2: Methyl (R)-3-amino-2-piperidin-1-ylpropanoate dihydrochloride 3.7 g (12.9 mmol) of methyl (R)-3-tert-butoxycarbonylamino-2-piperidin-1-ylpropanoate are placed in a mixture of 25 ml of methanol and 15 ml of hydrochloric acid in solution in isopropanol having a concentration of 5-6N. The reaction medium is stirred at 40° C. for 18 h and then concentrated under vacuum. 3.5 g (100%) of methyl(S)-3-amino-2-piperidin-1-ylpropanoate dihydrochloride are obtained in the form of a beige solid.

16.3: Sodium salt of 4-(2-methylquinolin-4-ylmethoxy)benzenesulfonic acid 100 g (438 mmol) of 4-chloromethyl-2-methylquinoline hydrochloride are added to a solution of 77 g (395 mmol) of the sodium salt of 4-hydroxybenzenesulfonic acid and of 84 ml (84 mmol) of an aqueous solution of sodium hydroxide, having a concentration of 1M, in 800 ml of isopropanol. The reaction medium is heated at 70° C. for 5 h and then at 40° C. for 18 h.

After evaporation of the isopropanol, the product obtained is filtered, rinsed with isopropanol and with diethyl ether and then dried under vacuum. 114 g (75%) of the sodium salt of 4-(2-methylquinolin-4-ylmethoxy)benzenesulfonic acid are obtained in the form of a white solid.

16.4: 4-(2-Methylquinolin-4-ylmethoxy)benzenesulfonyl chloride 76 g (216 mmol) of the sodium salt of 4-(2-methylquinolin-4-ylmethoxy)benzenesulfonic acid in 500 ml of dimethylformamide are added dropwise to a solution of 55 ml (649 mmol) of oxalyl chloride in 100 ml of dichloromethane, cooled beforehand to −10° C. After the addition, the reaction medium is stirred at ambient temperature for 18 h. The reaction medium is then poured into 1 l of ice and then extracted with ethyl acetate. The organic phases are combined, washed with water and then with a saturated aqueous solution of sodium chloride, dried over magnesium sulfate, filtered and concentrated under vacuum. 77 g (92%) of 4-(2-methylquinolin-4-ylmethoxy)benzenesulfonyl chloride hydrochloride are obtained in the form of a beige solid.

16.5: Methyl (R)-3-[4-(2-methylquinolin-4-ylmethoxy)benzenesulfonylamino]-2-piperidin-1-ylpropanoate 7.2 ml (51.5 mmol) of triethylamine and then 5.9 g (15.5 mmol) of 4-(2-methylquinolin-4-ylmethoxy)-benzenesulfonyl chloride hydrochloride are added to a solution of 3.34 g (12.9 mmol) of methyl (R)-3-amino-2-piperidin-1-ylpropanoate dihydrochloride in 30 ml of dichloromethane and 30 ml of dimethylformamide cooled beforehand using an ice bath. The reaction medium is stirred at ambient temperature for 3 h 30, hydrolyzed, and then diluted with dichloromethane. The product is extracted with dichloromethane. The organic phase is washed with water, dried over magnesium sulfate, filtered and concentrated under vacuum. The residue obtained is purified by chromatography on silica gel, elution being carried out with a 50/50 heptane/ethyl acetate mixture. 4 g (62%) of methyl (R)-3-[4-(2-methylquinolin-4-ylmethoxy)benzenesulfonylamino]-2-piperidin-1-ylpropanoate are obtained in the form of a white solid.

16.6: (R)-3-[4-(2-methylquinolin-4-ylmethoxy)benzenesulfonylamino]-2-piperidin-1-ylpropanoic acid In a manner analogous to example 1.6, using 4.0 g (8.0 mmol) of methyl (R)-3-[4-(2-methylquinolin-4-ylmethoxy)

benzenesulfonylamino]-2-piperidin-1-ylpropanoate, 2.95 g (76%) of (R)-3-[4-(2-methylquinolin-4-ylmethoxy)benzenesulfonylamino]-2-piperidin-1-ylpropanoic acid are obtained in the form of a white solid.

16.7: (R)—N-hydroxy-3-[4-(2-methylquinolin-4-ylmethoxy)benzenesulfonylamino]-2-piperidin-1-yl-propionamide In a manner analogous to example 1.7, using 2.95 g (6 mmol) of (R)-3-[4-(2-methylquinolin-4-ylmethoxy)benzenesulfonylamino]-2-piperidin-1-ylpropanoic acid, 1.8 g of crude residue are obtained and recrystallized from a 50/50 acetone/water mixture. After filtration, the solid obtained is again purified by chromatography on silica gel, elution being carried out with a 95/5 dichloromethane/methanol mixture. 50 mg (2%) of (R)—N-hydroxy-3-[4-(2-methylquinolin-4-ylmethoxy)-benzenesulfonylamino]-2-piperidin-1-ylpropionamide are obtained in the form of a beige solid.

$^1$H NMR (δ, DMSO): 1.29-1.31 (m, 2H); 1.39-1.40 (m, 4H); 2.34-2.38 (m, 4H); 2.67 (s, 3H); 2.73-2.79 (m, 1H); 2.96-2.99 (m, 2H); 5.72 (s, 2H); 7.33-7.37 (m, 3H); 7.57-7.62 (m, 2H); 7.74-7.80 (m, 1H); 7.98 (d, J=8.4 Hz, 2H); 8.11 (d, J=8.4 Hz, 2H); 8.86 (s, 1H), 10.54 (s, 1H).

Example 17

Enzymatic Assay for TACE Inhibition

Description of the Assay

The products are solubilized in DMSO at a concentration of 10 mM. A serial 3-fold dilution over 10 points is carried out so as to have a concentration range of from 10 μM to 0.5 nM final concentration. The TACE enzyme is an internal production (carried out according to the publication "protein Eng Des Sel 2006, 19,155-161") and is added so as to have a signal equivalent to 6 times the background noise in 2 h at 37° C. The reaction is carried out in 50 mM Tris buffered medium containing 4% glycerol, pH 7.4. The fluorescent substrate is MCA-Pro-Leu-Ala-Val-(Dpa)-Arg-Ser-Ser-Arg-NH$_2$ (R&D systems, reference: ES003). The substrate is cleaved by the enzyme between the alanine and the valine, thus releasing a fluorescent peptide (excitation: 320 nm, emission: 420 nm). The substrate is used at 40 μM. The reaction is carried out in a final volume of 10 μl (4 μl inhibitor, 4 μl substrate, 2 μl enzyme) in a low volume 384-well plate (Corning reference: 3676). The plate is incubated at ambient temperature for 2 h, and then read by fluorescence on a Pherastar reader (BMG labtech). The IC$_{50}$ is determined using mathematical processing software (XLfit).

Product Assay

| Example No. | % TACE inhibition at 10 μM | IC$_{50}$-TACE (nM) |
| --- | --- | --- |
| Ex. 1 | 98 | 181 |
| Ex. 2 | 95 | 298 |
| Ex. 3 | 97 | 181 |
| Ex. 5 | 97 | 249 |
| Ex. 6 | 97 | 328 |
| Ex. 7 | 98 | 147 |
| Ex. 8 | 99 | 26 |
| Ex. 9 | 99 | 469 |
| Ex. 14 | 91 | 38 |
| Ex. 15 | 98 | 112 |

On the basis of the results obtained in the TACE enzymatic assay described above, the compounds claimed in the present invention are TNF-alpha converting enzyme (TACE) inhibitors and consequently may be potential active ingredients for the treatment of pathological conditions for which reducing TNF-alpha production would be of great interest.

Example 18

Selectivity Assay

Principle of the Assay:

The molecules are dose-response tested on the following enzymes: MMP1, MMP3, MMP9, ADAM9 and ADAM10, according to the same protocol as that described for the TACE enzyme in example 17, but with different substrates (MMP R&D systems, reference: P126-990, and ADAM R&D systems, reference: ES003).

The enzymes are purchased from Calbiochem.

Product Assay:

| | IC50 (nM) | | | | | |
| --- | --- | --- | --- | --- | --- | --- |
| Example | MMP1 | MMP3 | MMP9 | ADAM9 | ADAM10 | TACE |
| 8 | 3000 | 4500 | >10000 | >10000 | >10000 | 26 |
| 14 | 1983 | 3034 | >10000 | >10000 | >10000 | 24 |
| Apratastat | 145 | 10 | 82 | 85 | 71 | 5 |

On the basis of the results obtained in the selectivity assay described above, these compounds are also very selective for TACE compared with the other ADAMs and MMPs, i.e. they have IC$_{50}$ values for other ADAMs or MMPs that are at least 10 times higher than that obtained for TACE, and more advantageously at least 100 times higher.

As it happens, insofar as it is known that the nonselective inhibition of these families of enzymes induces adverse side effects observed in vivo, the selective inhibition of TACE compared with these other enzymes should make it possible to reduce adverse side effects when these molecules are administered for the treatment of pathological conditions for which reducing TNF-alpha production would be of great interest.

The invention claimed is:

1. A compound of formula (I) below:

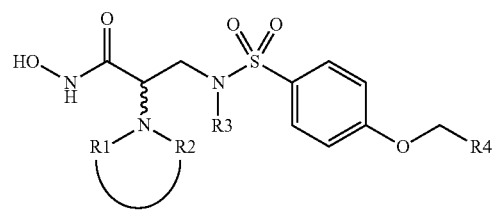

in which:

R$_1$ and R$_2$ are identical or different and represent alkyl radicals or else they form a ring with the nitrogen atom to which they are attached, said ring being represented by the formula below:

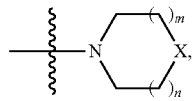

X, m, and n having the meanings given hereinafter;

$R_3$ is a hydrogen atom or a lower alkyl radical;

$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical, or a substituted heteroaralkyl radical;

X represents an oxygen atom, a —$CH_2$— radical, a —CH—$(CH_2)$p-$NR_5R_6$ radical, a sulfur atom, an SO radical, or an $SO_2$ radical, with $R_5$, $R_6$, and p having the meanings given hereinafter;

$R_5$ and $R_6$, which are identical or different, represent a hydrogen atom, an alkyl radical, a substituted alkyl radical, an aryl radical, or a substituted aryl radical;

m can take the values of 0 or 1;

n can take the values of 0, 1, 2, or 3; and p can take the values of 0, 1, or 2;

and also addition salts of the compound of formula (I) with a pharmaceutically acceptable acid, addition salts of the compound of formula (I) with a pharmaceutically acceptable base, and enantiomers of the compound of formula (I).

2. The addition salts of the compound as claimed in claim 1, with a pharmaceutically acceptable acid, wherein the pharmaceutically acceptable acid is selected from the group consisting of hydrochloric acid, hydrobromic acid, sulfuric acid, nitric acid, phosphoric acid, acetic acid, trifluoroacetic acid, trichloroacetic acid, propionic acid, glycolic acid, pyruvic acid, succinic acid, benzoic acid, cinnamic acid, mandelic acid, methanesulfonic acid, para-toluenesulfonic acid, salicylic acid, picric acid, citric acid, oxalic acid, tartaric acid, malonic acid, maleic acid, camphorsulfonic acid, and fumaric acid.

3. The addition salts of the compound as claimed in claim 1, with a pharmaceutically acceptable base, wherein the pharmaceutically acceptable base is selected from the group consisting of potassium hydroxide, sodium hydroxide, lithium hydroxide, calcium hydroxide, methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline, isoquinoline, lysine, arginine, and ornithine.

4. The compound as claimed in claim 1, wherein, $R_1$ and $R_2$, which are identical or different, represent alkyl radicals or else they form a ring with the nitrogen atom to which they are attached, said ring being represented by the formula below:

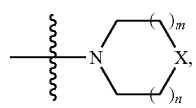

X, m, and n having the meanings given hereinafter;

$R_3$ is a hydrogen atom or a lower alkyl radical;

$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical, or a substituted heteroaralkyl radical;

X represents an oxygen atom, a —$CH_2$— radical, a —CH—$(CH_2)$p-$NR_5R_6$ radical, a sulfur atom, an SO radical, or an $SO_2$ radical, with $R_5$, $R_6$, and p having the meanings given hereinafter;

$R_5$ and $R_6$, which are identical or different, represent a hydrogen atom, an alkyl radical, a substituted alkyl radical, an aryl radical, or a substituted aryl radical;

m can take the values of 0 or 1;

n can take the values of 0, 1, or 2; and p can take the values of 0, 1, or 2;

and also addition salts of the compound with a pharmaceutically acceptable acid, addition salts of the compound with a pharmaceutically acceptable base, and enantiomers of the compound.

5. The compound as claimed in claim 1, wherein, $R_1$ and $R_2$ are identical or different and represent alkyl radicals or else they form a ring with the nitrogen atom to which they are attached, said ring being represented by the formula below:

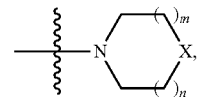

X, m, and n having the meanings given hereinafter;

$R_3$ is a hydrogen atom or a lower alkyl radical;

$R_4$ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical, or a substituted heteroaralkyl radical;

X represents an oxygen atom, a —$CH_2$— radical, or a —CH—$(CH_2)$p-$NR_5R_6$ radical, with $R_5$, $R_6$ and p having the meanings given hereinafter; $R_5$ and $R_6$, which are identical or different, represent a hydrogen atom, an alkyl radical, a substituted alkyl radical, an aryl radical, or a substituted aryl radical;

m takes the value of 1;

n can take the values of 0, 1, or 2; and p can take the values of 0, 1, or 2;

and also addition salts of the compound with a pharmaceutically acceptable acid, addition salts of said compound with a pharmaceutically acceptable base, and enantiomers of the compound.

6. The compound as claimed in claim 1, wherein, $R_1$ and $R_2$ are identical or different and form a ring with the nitrogen atom to which they are attached, said ring being represented by the formula below:

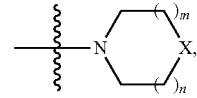

X, m, and n having the meanings given hereinafter;

$R_3$ is a hydrogen atom;

R₄ is an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical, or a substituted heteroaralkyl radical;

X represents an oxygen atom, a —CH₂ radical, or a —CH—(CH₂)p-NR₅R₆ radical, with R₅, R₆, and p having the meanings given hereinafter;

R₅ and R₆, which are identical or different, represent a hydrogen atom, an alkyl radical, a substituted alkyl radical, an aryl radical, or a substituted aryl radical;

m takes the value of 1;

n can take the values of 1 or 2; and p can take the values of 0, 1, or 2;

and also addition salts of the compound with a pharmaceutically acceptable acid, addition salts of the compound with a pharmaceutically acceptable base, and enantiomers of the compound.

7. The compound as claimed in claim 1,
wherein,
R₁ and R₂ are identical or different and form a ring with the nitrogen atom to which they are attached, said ring being represented by the formula below:

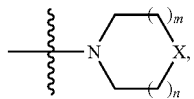

X, m, and n having the meanings given hereinafter;
R₃ is a hydrogen atom;
R₄ is a heterocyclic radical, a substituted heterocyclic radical, a heteroaryl radical, a substituted heteroaryl radical, a heteroaralkyl radical, or a substituted heteroaralkyl radical;
X represents an oxygen atom or a —CH₂ radical;
m takes the value of 1; and
n takes the value of 1;
and also addition salts of the compound with a pharmaceutically acceptable acid, addition salts of the compound with a pharmaceutically acceptable base, and enantiomers of the compound.

8. The compound as claimed in claim 1,
wherein,
R₁ and R₂ are identical or different and form a ring with the nitrogen atom to which they are attached, said ring being represented by the formula below:

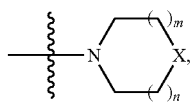

X, m, and n having the meanings given hereinafter;
R₃ is a hydrogen atom;
R₄ is a heteroaryl radical or a substituted heteroaryl radical;
X represents an oxygen atom or a —CH₂ radical;
m takes the value of 1; and
n takes the value of 1;
and also addition salts of the compound with a pharmaceutically acceptable acid, addition salts of the compound with a pharmaceutically acceptable base, and enantiomers of the compound.

9. A compound, addition salts of the compound with a pharmaceutically acceptable acid, addition salts of the compound with a pharmaceutically acceptable base, and enantiomers of the compound, wherein the compound is selected from the group consisting of:

1) (S)-3-(4-benzyloxybenzenesulfonylamino)-N-hydroxy-2-piperidin-1-ylpropionamide;
2) (S)-3-(4-benzyloxybenzenesulfonylamino)-N-hydroxy-2-pyrrolidin-1-ylpropionamide;
3) (S)-3-[4-(4-fluorobenzyloxy)benzenesulfonylamino]-N-hydroxy-2-piperidin-1-ylpropionamide;
4) (S)-3-[(4-benzyloxybenzenesulfonyl)methylamino]-N-hydroxy-2-piperidin-1-ylpropionamide;
5) (S)—N-hydroxy-3-[4-(naphthalen-2-ylmethoxy)benzenesulfonylamino]-2-piperidin-1-ylpropionamide;
6) (S)-3-[4-(3,4-dichlorobenzyloxy)benzenesulfonylamino]-N-hydroxy-2-piperidin-1-ylpropionamide;
7) (S)-3-(4-benzyloxybenzenesulfonylamino)-N-hydroxy-2-morpholin-4-ylpropionamide;
8) (S)—N-hydroxy-3-[4-(2-methylquinolin-4-ylmethoxy)benzenesulfonylamino)-2-piperidin-1-ylpropionamide;
9) (S)-3-(4-(3,5-dichlorobenzyloxy)benzenesulfonylamino]-N-hydroxy-2-piperidin-1-ylpropionamide;
10) (S)—N-hydroxy-2-piperidin-1-yl-3-(4-propoxybenzenesulfonylamino)propionamide;
11) (S)-3-(4-cyclopropylmethoxybenzenesulfonylamino)-N-hydroxy-2-morpholin-4-ylpropionamide;
12) (S)-3-[4-(4-tert-butylbenzyloxy)benzenesulfonylamino]-N-hydroxy-2-morpholin-4-ylpropionamide;
13) (S)—N-hydroxy-2-morpholin-4-yl-3-(4-phenethyloxybenzenesulfonylamino)propionamide;
14) (S)—N-hydroxy-3-[4-(2-methylquinolin-4-ylmethoxy)benzenesulfonylamino]-2-morpholin-4-yl-propionamide;
15) (S)—N-hydroxy-3-[4-(2-methylquinolin-4-ylmethoxy)benzenesulfonylamino]-2-piperidin-1-ylpropionamide;
16) (R)—N-hydroxy-3-[4-(2-methylquinolin-4-ylmethoxy)benzenesulfonylamino]-2-pyrrolidin-1-ylpropionamide;
17) (R)—N-hydroxy-3-(4-(2-methylquinolin-4-ylmethoxy)benzenesulfonylamino-2-piperidin-1-yl-propionamide;
18) (S)—N-hydroxy-3-[4-(2-methylquinolin-4-ylmethoxy)benzenesulfonylamino]-2-thiomorpholin-4-yl-propionamide;
19) (S)-2-(1,1-dioxothiomorpholin-4-yl)-N-hydroxy-3-[4-(2-methylquinolin-4-ylmethoxy)benzenesulfonylamino]propionamide;
20) (S)-2-diethylamino-N-hydroxy-3-[4-(2-methylpyridin-4-ylmethoxy)benzenesulfonylamino]-propionamide;
21) (S)-3-[4-(2,6-dimethylpyridin-4-ylmethoxy)benzenesulfonylamino]-2-(ethylpropylamino)-N-hydroxy-propionamide;
22) (S)-2-azepan-1-yl-N-hydroxy-3-[4-(3-methylbenzyloxy)benzenesulfonylamino]propionamide;
23) (S)-2-azepan-1-yl-N-hydroxy-3-[4-(2-methylquinolin-4-ylmethoxy)benzenesulfonylamino]-propionamide;
24) (S)—N-hydroxy-2-piperidin-1-yl-3-[4-(pyrazolo[1,5-a]pyridin-3-ylmethoxy)benzenesulfonylamino]-propionamide;
25) (S)—N-hydroxy-3-[4-(2-methylpyrazolo[1,5-a]pyridin-3-ylmethoxy)benzenesulfonylamino]-2-piperidin-1-ylpropionamide;

26) (S)—N-hydroxy-2-piperidin-1-yl-3-[4-(quinolin-4-ylmethoxy)benzenesulfonylamino]propionamide;
27) (S)—N-hydroxy-2-morpholin-4-yl-3-[4-(quinolin-4-ylmethoxy)benzenesulfonylamino]propionamide;
28) (S)—N-hydroxy-3-{propyl[4-(quinolin-4-ylmethoxy)benzenesulfonyl]amino}-2-pyrrolidin-1-yl-propionamide;
29) (S)-2-diethylamino-N-hydroxy-3-[4-(quinolin-4-ylmethoxy)benzenesulfonylamino]propionamide;
30) (S)—N-hydroxy-3-[4-(3-methylbenzyloxy)benzenesulfonylamino]-2-[1,4]-oxazocan-4-yl-propionamide;
31) (S)-2-azocan-1-yl-N-hydroxy-3-[4-(pyrimidin-4-ylmethoxy)benzenesulfonylamino]propionamide;
32) (S)—N-hydroxy-2-morpholin-4-yl-3-[4-(pyrazolo[1,5-a]pyridin-3-ylmethoxy)benzenesulfonylamino]-propionamide;
33) (S)—N-hydroxy-3-[4-(pyrazolo[1,5-a]pyridin-3-ylmethoxy)benzenesulfonylamino]-2-thiomorpholin-4-ylpropionamide;
34) (S)—N-hydroxy-2-piperidin-1-yl-3-[4-(4-propoxybenzyloxy)benzenesulfonylamino]propionamide;
35) (R)—N-hydroxy-3-[4-(2-methylquinolin-4-ylmethoxy)benzenesulfonylamino]-2-morpholin-4-yl-propionamide;
36) (S)-2-(4-ethylaminopiperidin-1-yl)-N-hydroxy-3-[4-(2-methylquinolin-4-ylmethoxy)benzenesulfonylamino]propionamide;
37) (S)-2-(3-aminopyrrolidin-1-yl)-N-hydroxy-3-[4-(2-methylquinolin-4-ylmethoxy)benzenesulfonylamino]propionamide;
38) (S)-2-(3-dimethylaminomethylpyrrolidin-1-yl)-N-hydroxy-3-[4-(2-methylquinolin-4-ylmethoxy)benzenesulfonylamino]propionamide;
39) (S)-2-(4-benzylaminopiperidin-1-yl)-N-hydroxy-3-[4-(2-methylpyridin-4-ylmethoxy)benzenesulfonylamino]propionamide;
40) (S)—N-hydroxy-3-[4-(2-methyl-1H-indol-3-ylmethoxy)benzenesulfonylamino]-2-piperidin-1-yl-propionamide;
41) (S)—N-hydroxy-3-[4-(2-isopropylbenzofuran-3-ylmethoxy)benzenesulfonylamino]-2-morpholin-4-yl-propionamide; and
42) (S)-2-azetidin-1-yl-N-hydroxy-3-[4-(2-methylquinolin-4-ylmethoxy)benzenesulfonylamino]-propionamide.

10. A pharmaceutical composition comprising the compound of claim 1, addition salts of the compound with a pharmaceutically acceptable acid, addition salts of the compound with a pharmaceutically acceptable base, or enantiomers of the compound, and a pharmaceutically acceptable carrier.

11. A method of treating a disease or disorder involving TNF-α production, wherein the method comprises administering the pharmaceutical composition as claimed in claim 10), to a subject to inhibit the production of TNF-α in the subject, wherein the disease or disorder is selected from the group consisting of septic shock, hemodynamic shock, malaria, inflammatory bowel disease (IBD), inflammatory bone disease, mycobacterial infections, meningitis, fibrotic disease, ischemic attack, transplant rejection, atherosclerosis, obesity, disease involving angiogenesis phenomena, osteoarthritis, rheumatoid arthritis, ankylosing spondylitis, juvenile chronic arthritis, multiple sclerosis, HIV, non-insulin-dependent diabetes mellitus, allergic diseases, asthma, chronic obstructive pulmonary disease (COPD), ocular inflammation, inflammatory skin disease, psoriasis, atopic dermatitis, psoriatic arthritis, Crohn's disease, and ulterative colitis.

12. A method of treating a disease or disorder involving TNF-α production, wherein the method comprises administering the pharmaceutical composition as claimed in claim 10, to a subject to inhibit the production of TNF-α in the subject, wherein the disease or disorder is selected from the group consisting of Parkinson's disease, amyotrophic lateral sclerosis, autoimmune diseases of the nervous system, autonomic diseases of the nervous system, dorsal pain, cerebral edema, cerebrovascular disorders, dementia, nervous system nerve fiber demyelinating autoimmune diseases, diabetic neuropathies, encephalitis, encephalomyelitis, epilepsy, chronic fatigue syndrome, giant cell arteritis, Guillain-Barre syndrome, headaches, multiple sclerosis, neuralgia, peripheral nervous system diseases, polyneuropathies, polyradiculoneuropathy, radiculopathy, respiratory paralysis, spinal cord diseases, Tourette's syndrome, central nervous system vasculitis, Huntington's disease, and stroke.

13. The method of claim 11, wherein the subject is a human or an animal.

14. A method of inhibiting the activity of TACE, comprising contacting a TACE with the pharmaceutical composition of claim 10.

15. A method of inhibiting the production of TNFα, comprising contacting a cell producing TNF-α with the pharmaceutical composition of claim 10.

16. A method of inhibiting a MMP, wherein the method comprises contacting the MMP with the pharmaceutical composition of claim 10.

17. The method of claim 16, wherein the MMP is MMP1 or MMP3.

18. The compound of claim 1, addition salts of the compound with a pharmaceutically acceptable acid, addition salts of the compound with a pharmaceutically acceptable base, and enantiomers of the compound, wherein the compound is (S)—N-hydroxy-3-[4-(2-methylquinolin-4-ylmethoxy)benzenesulfonylamino]-2-piperidin-1-ylpropionamide or (S)—N-hydroxy-3-[4-(2-methylquinolin-4-ylmethoxy)benzenesulfonylamino]-2-morpholin-4-yl-propionamide.

19. A pharmaceutical composition comprising the compound of claim 18, addition salts of the compound with a pharmaceutically acceptable acid, addition salts of the compound with a pharmaceutically acceptable base, or enantiomers of the compound, and a pharmaceutically acceptable carrier.

20. The method of claim 12, wherein the subject is a human or an animal.

* * * * *